US005455870A

United States Patent [19]
Sepai et al.

[11] Patent Number: 5,455,870
[45] Date of Patent: Oct. 3, 1995

[54] APPARATUS AND METHOD FOR INSPECTION OF HIGH COMPONENT DENSITY PRINTED CIRCUIT BOARD

[75] Inventors: Dinyar Sepai, Framingham; Kevin R. Daly, Stow; Brian L. Whalen, Grafton; Khanh Hong, Ashland; George B. Jones, Stow, all of Mass.

[73] Assignee: Raytheon Company, Lexington, Mass.

[21] Appl. No.: 265,567

[22] Filed: Jun. 24, 1994

Related U.S. Application Data

[60] which is a continuation of Ser. No. 83,212, Jun. 25, 1993, abandoned, which is a continuation of Ser. No. 727,758, Jul. 10, 1991, abandoned.

[51] Int. Cl.$^6$ .............................. G06K 9/00; G01N 21/32
[52] U.S. Cl. .................... 382/147; 356/237; 348/126; 348/131; 382/149; 382/150
[58] Field of Search .................. 382/8, 18; 356/237, 356/376, 273; 250/563, 562; 348/126, 131

[56] References Cited

U.S. PATENT DOCUMENTS

| | | | |
|---|---|---|---|
| 4,343,553 | 8/1982 | Nakagawa et al. | 356/376 |
| 4,538,909 | 9/1985 | Bible et al. | 356/237 |
| 4,677,473 | 6/1987 | Okamoto et al. | 358/101 |
| 4,688,939 | 8/1987 | Ray | 356/237 |
| 4,696,104 | 9/1987 | Vanzetti et al. | 29/840 |
| 4,809,308 | 2/1989 | Adams et al. | 378/99 |

(List continued on next page.)

OTHER PUBLICATIONS

Rajarshi, Ray, "Automated Inspection of Solder Bumps Using Visual Signatures of Specular Image–Highlights", IEEE, 1989, pp. 588–596, Princeton, N.J.
"Standard Requirements for Soldered Electrical and Electronic Assemblies," Department of Defense, MIL–STD= 2000, Jan. 16, 1989, pp. i–vii and 1–31.
"A Three–Dimensional Approach to Automatic Solder Joint Inspection," Sullivan S. Chen, Robotic Vision Systems, Inc., Hauppauge, N.Y., pp. 1–4.
"Digital Image Processing," William K. Pratt, John Wiley and Sons, Inc., second edition, 1991., pp. 491, 497–512, 514–517.
Blanz et al., "Image Analysis Methods for Solder–Ball Inspection in Integrated Circuit Manufacturing", IEEE, 1988, pp. 129–139.

*Primary Examiner*—Leo H. Boudreau
*Assistant Examiner*—Matthew C. Bella
*Attorney, Agent, or Firm*—Walter F. Dawson

[57] ABSTRACT

An automated electronic module inspection system having illumination sources that produce digitized gray scale images that are then analyzed by a computer. The inspection system illuminates the module including solder joints, components and printed circuit board using a sequence of illumination that produce visual images which are used to identify defects. The inspection system inspects for all defects as specified in MIL-STD-2000A (Section 4.4) by using both surface reflectance properties as well as topological properties of objects. The system comprises two video cameras. A positioning table aligns a module-under-test with the optical axis of each camera thereby enabling the same field-of-view to be observed under different lighting conditions. A dark field illumination associated with a first camera preferentially illuminates non-flat surfaces, but not vertical surfaces. A bright field illumination associated with a second camera preferentially illuminates relatively flat surfaces. The flat-surface illumination light source is collimated with the optical axis of the camera using a conventional partially reflecting angled mirror that reflects the light along the camera's optical axis onto a circuit board of the module. The angled surfaces are illuminated using four ring-lights concentrically aligned with the optical axis of the second camera. The images observed by the camera are then analyzed by inspection programs for discrepancies between image model attributes and the images, and such programs provide compensation for nonuniformities of the light sources and cameras and compensation of shadows resulting from the dark field illumination light source.

52 Claims, 13 Drawing Sheets

U.S. PATENT DOCUMENTS

| | | | |
|---|---|---|---|
| 4,876,455 | 10/1989 | Sanderson et al. | 250/560 |
| 4,926,452 | 5/1990 | Baker et al. | 378/22 |
| 4,988,202 | 1/1991 | Nayar et al. | 356/394 |
| 4,999,285 | 3/1991 | Schmuter | 382/8 |
| 5,015,097 | 5/1991 | Nomoto et al. | 356/394 |
| 5,030,008 | 7/1991 | Scott et al. | 356/394 |
| 5,039,868 | 8/1991 | Kobayashi et al. | 250/572 |
| 5,058,178 | 10/1991 | Ray | 382/8 |
| 5,060,065 | 10/1991 | Wasserman | 358/106 |
| 5,127,726 | 7/1992 | Moran | 356/237 |
| 5,247,344 | 9/1993 | Doan | 356/394 |

APPARATUS AND METHOD FOR INSPECTION OF HIGH COMPONENT DENSITY PRINTED CIRCUIT BOARD

This application is a continuation of application Ser. No. 08/083,212 filed Jun. 25, 1993, now abandoned, which is a continuation of application Ser. No. 07/727,758, filed Jul. 10, 1991, now abandoned.

BACKGROUND OF THE INVENTION

This invention relates to the inspection of solder joints and more particularly to an apparatus and method for performing automated visual inspection of solder joints on printed circuit boards using surface mount technology (SMT).

Visual inspection of individual solder joints checks for correct mechanical (physical) attributes which are characterized by the topology of the joint and the correct photometric (finish) attributes which are characterized by the reflectivity of the joint. Automated inspection machines in the prior art address either the inspection of photometric attributes or the inspection of mechanical attributes, but not both. Such prior art inspection machines comprises either radiographic methods, X-ray laminographic methods, thermal reflectance methods, visible light spectrum reflectance methods, optical or triangulation methods. However, each of the methods used for inspection have fundamental deficiencies that make them unsuitable for meeting all the inspection requirements in Section 4.4 of Military Standard MIL-STD-2000A, "Standard Requirements for Soldered Electrical and Electronic Assemblies", Department of Defense, USA, which includes not only inspection for defects in the solder joints (mechanical and photometric attributes) but also the condition of the printed circuit board and mounted devices.

Radiographic images represent the x-ray transmittance properties of solder joints. U.S. Pat. No. 4,809,308, issued on Feb. 28, 1989, to John Adams et al. entitled "Method and Apparatus For Performing Automated Circuit Board Solder Quality Inspection" and assigned to IRT Corporation describes a method and apparatus for measuring structural characteristics of a manufactured circuit board containing solder joints by automated real-time digital X-ray radiographic inspection techniques. This technique cannot extract any information of the surface reflectance or topological properties of the joint.

U.S. Pat. No. 4,926,452, issued on May 15, 1990, to Bruce D. Baker et al. entitled "Automated Laminography System for Inspection of Electronics" and assigned to Four PI Systems Corporation, discloses a laminography system for inspecting electrical connections by producing crosssectional images of the connections which are then analyzed by a computer aided image analysis system. X-ray laminograph images represent the transmittance property of a horizontal cross-section of the solder joint. A multitude of cross-sections would represent the topology properties of the joint. However, the method cannot convey surface reflectance properties of the solder joint.

Thermal reflectance techniques use active methods to detect the cumulative near infrared energy radiated from a solder joint with respect to time. U.S. Pat. No. 4,696,104, issued on Sep. 29, 1987, to Riccardo Vanzetti et al. entitled "Method and Apparatus for Placing and Electrically Connecting Components on a Printed Circuit Board" and assigned to Vanzetti System Inc., describes a system that checks the quality of a solder joint Using an infrared detector to sense the thermal radiation from the heated solder material during cool down which provides a signal for comparison with a standard signal signature. However, no inferences can be made about the precise topology or surface reflectance properties of the joint since an image is not acquired. Also, the technique is unable to identify minor (spatially localized) impurities.

Optical triangulation methods construct a detailed topology of the solder joint. An article entitled "A Three-dimensional Approach to Automatic Solder Inspection" by Sullivan S. Chen, Electronic Manufacturing, November 1988, describes a three-dimensional (3D) vision system manufactured by Robotic Vision Systems Incorporated, using optical triangulation and image processing techniques based on structured light and software having rules based on theoretical and expert knowledge about what makes a joint good or defective. No decision is based on absolute comparisons but on a multitude of measurements and the relationship between them. However, the method is unable to extract reflectance properties of such joints. Also, the extraction of data relies on precise calibration of the printed circuit board plane, without which topology representation would be precarious.

U.S. Pat. No. 4,876,455, issued on Oct. 24, 1989 to Arthur C. Sanderson et al. entitled "Fiber Optic Solder Joint Inspection System" and assigned to Westinghouse Electric Corporation, discloses a method and apparatus for determining the topology of an object having a specular surface using a series of point light sources and associated reflections from the object surface to detect light patterns which are interpreted and used to reconstruct the object surface through curve fitting; a rule-based system through comparison with acceptable solder joint surface features, evaluates and classifies the joint for an acceptable determination. U.S. Pat. No. 4,988,202, issued on Jan. 29, 1991, to Shree K. Nayar et al., entitled "Solder Joint Inspection System and Method" and assigned to Westinghouse Electric Corporation, discloses a similar system as in Sanderson et al., where the surface reflections of the joint are utilized to generate an Extended Gaussian Image representation of the joint which is then evaluated to determine the joint acceptability. However, these techniques are not robust for evaluating photometric attributes because data inference made through curve fitting can overlook small defects.

U.S. Pat. No. 4,688,939, issued on Aug. 25, 1987, to Rajarshi Ray, entitled "Method and Apparatus for Inspecting Articles" and assigned to AT&T Technologies, Incorporated, discloses a method and apparatus for inspecting a chip carrier for the presence of light-reflective solder bumps using a ring lamp, a television camera, and a vision system coupled to the television camera for creating a one-dimensional profile of intensity of the image for each window which is then analyzed to detect for defects by examining the spacing and characteristics of the peaks in such window. However, this system requires a very high resolution camera in order to detect small defects because of its one-dimensional inspection characteristics. It also does not have the capability for printed circuit board inspection, and it only addresses solder bumps, i.e., hemispherical surfaces.

The present invention of an Automated Vision Inspection System is capable of inspecting for all defect categories called for in Section 4.4 of MIL-STD-2000A.

SUMMARY OF THE INVENTION

Accordingly, it is therefore an object of this invention to use a visual spectrum sensor to view a solder joint in order to extract reflectance properties as well as topological properties.

It is a further object of this invention to perform an automated visual inspection of all solder joints on a surface mounted technology printed circuit board which is capable of identifying all defect categories specified in Section 4.4 of MIL-STD-2000A.

It is a further object of this invention to perform an automated visual inspection of a printed circuit board and the components thereon in accordance with the defect categories specified in Section 4.4 of MIL-STD-2000A.

The objects are further accomplished by providing an apparatus for inspection of an electronic module comprising means for positioning the module during the inspection, a first light source positioned in accordance with the positioning means above the module for illuminating the module, a first sensing means disposed above the first light source means for sensing an intensity of reflected light from the first light source to obtain a first image, a second light source positioned in accordance with the positioning means above the module for illuminating the module, a second sensing means disposed above the second light source means for sensing an intensity of reflected light from the second light source to obtain a second image, processing means for compensating the first image for nonuniformities resulting from the first light source and the first sensing means and for compensating the second image for nonuniformities resulting from the second light source and the second sensing means, the processing means further comprises means for compensating the first image for shadows from the first light source, means included in the processing means for performing a two dimensional intensity transformation on the first image and the second image for establishing a three-dimensional topography of the module, and means included in the processing means for analyzing the three-dimensional topography and the intensity of reflected light to determine the condition of the module. The first light source means comprises means for providing a dark field illumination to the non-flat surfaces of the module. The second light source means comprises means for providing a bright field illumination to the flat surfaces of the module. The means for performing a two-dimensional intensity transformation comprises conversion of the intensity transformation to a surface angle representation. The means for performing a two-dimensional intensity transformation comprises means for performing a gradient analysis, a component interconnect boundary detection, a supervised segmentation, an unsupervised segmentation and a circular feature identification on the first image and the second image for establishing the three-dimensional topography. The means for analyzing the three-dimensional topography comprises means for comparing the established three-dimensional topography to a predetermined three-dimensional topography criteria. The analyzing means comprises an expert system having a plurality of decision levels and in an alternate embodiment it may also comprise an expert system having a neural network. The expert system determines a defective condition of solder connections, components and printed circuit materials of the module.

The objects are further accomplished by providing an automated vision inspection system comprising a computer means for controlling the operation of the vision inspection system, a positioning table having a plurality of adjustable axes for positioning a module during an inspection in accordance with a command signal from the computer means, a dark field illumination means positioned above the module for illuminating non-flat surfaces of the module, a first camera disposed above the dark field illumination means and attached to a first Z-axis of the positioning table for sensing an intensity of reflected light from the module to obtain a first image, a bright field illumination means positioned above the module and adjacent to the dark field illumination means for illuminating flat surfaces of the module, a second camera disposed above the bright field illumination means and attached to a second Z-axis of the positioning table for sensing an intensity of reflected light from the module to obtain a second image, processing means within the computer means for compensating the first image for nonuniformities from the dark field illumination means and the first camera and for compensating the second image for nonuniformities resulting from the bright field illumination means and the second camera, means included in the processing means for performing a two-dimensional transformation on the first image and the second image for establishing a three-dimensional topography of the module, means for comparing the established three-dimensional topography to a predetermined three-dimensional topography criteria, and expert system means for analyzing the results of the comparing means to detect a defect in the module. The means for obtaining the first image and the second image comprises means for transferring the first image and the second image to the computer means. The compensating means further comprises means for compensating the first image for shadows from the dark field illumination means. The means for performing a two-dimensional intensity transformation comprises conversion of the intensity transformation to a surface angle representation. The means for performing a two-dimensional transformation comprises means for performing a gradient analysis, a component interconnect boundary detection, a supervised segmentation, an unsupervised segmentation, and a circular feature identification on the first image and the second image for establishing the three dimensional topography. The expert system means comprises a plurality of decision levels. The expert system means further comprises a neural network means. The expert system determines a defective condition of solder connections, components, and printed circuit materials of the module. The dark field illumination means comprises a plurality of ring lamps. The system further comprises means for individually activating each of the plurality of ring lamps in accordance with a control signal generated by the computer means. The system comprises means for activating the ring lamps simultaneously in accordance with a control signal generated by the computer means.

The objects are further accomplished by providing a method for inspection of an electronic module comprising the steps of positioning the module for the inspection with a positioning means having a plurality of axes, illuminating the module with a first light source, sensing an intensity of reflected light from the first light source with a first sensing means to obtain a first image, repositioning the module for the inspection, illuminating the module with a second light source, sensing an intensity of reflected light from the second light source with a second sensing means to obtain a second image, compensating in a processing means the first image for nonuniformities resulting from the first light source and the first sensing means, the second image for nonuniformities resulting from the second light source and the second sensing means, and compensating said first image for shadows from said first light source, performing in the processing means a two-dimensional intensity transformation on the first image and the second image for establishing a three-dimensional topography of the module, and analyzing the three-dimensional topography and the intensity of reflected light in the processing means to determine the condition of the module. The step of illuminating the module with a first light source comprises providing a dark field illumination to the surface of the module. The step of illuminating the module with a second light source comprises providing a bright field illumination to the surface of the module. The step of performing a two-dimensional intensity transformation comprises the step of converting of such intensity transformation to surface angle representation. The step of performing a two-dimensional topography transformation comprises the steps of performing a gradient analysis, a component interconnect boundary detection, a supervised segmentation, an unsupervised segmentation and a circular feature identification on the first image and the second image for establishing the three-dimensional topography. The step of analyzing the three-dimensional topography comprises the step of comparing the established three-dimensional topography to a predetermined three-dimensional topography criteria. The step of comparing the established three-dimensional typography to a predetermined three-dimensional criteria comprises the step of employing an expert system comprising a plurality of decision levels. The step of employing an expert system further comprises employing a neural network. The step of determining the condition of the module includes the condition of devices, solder connections and printed circuit materials.

BRIEF DESCRIPTION OF THE DRAWINGS

Other and further features and advantages of the invention will become apparent in connection with the accompanying drawings wherein.

DESCRIPTION OF THE PREFERRED EMBODIMENT

Figure 1:
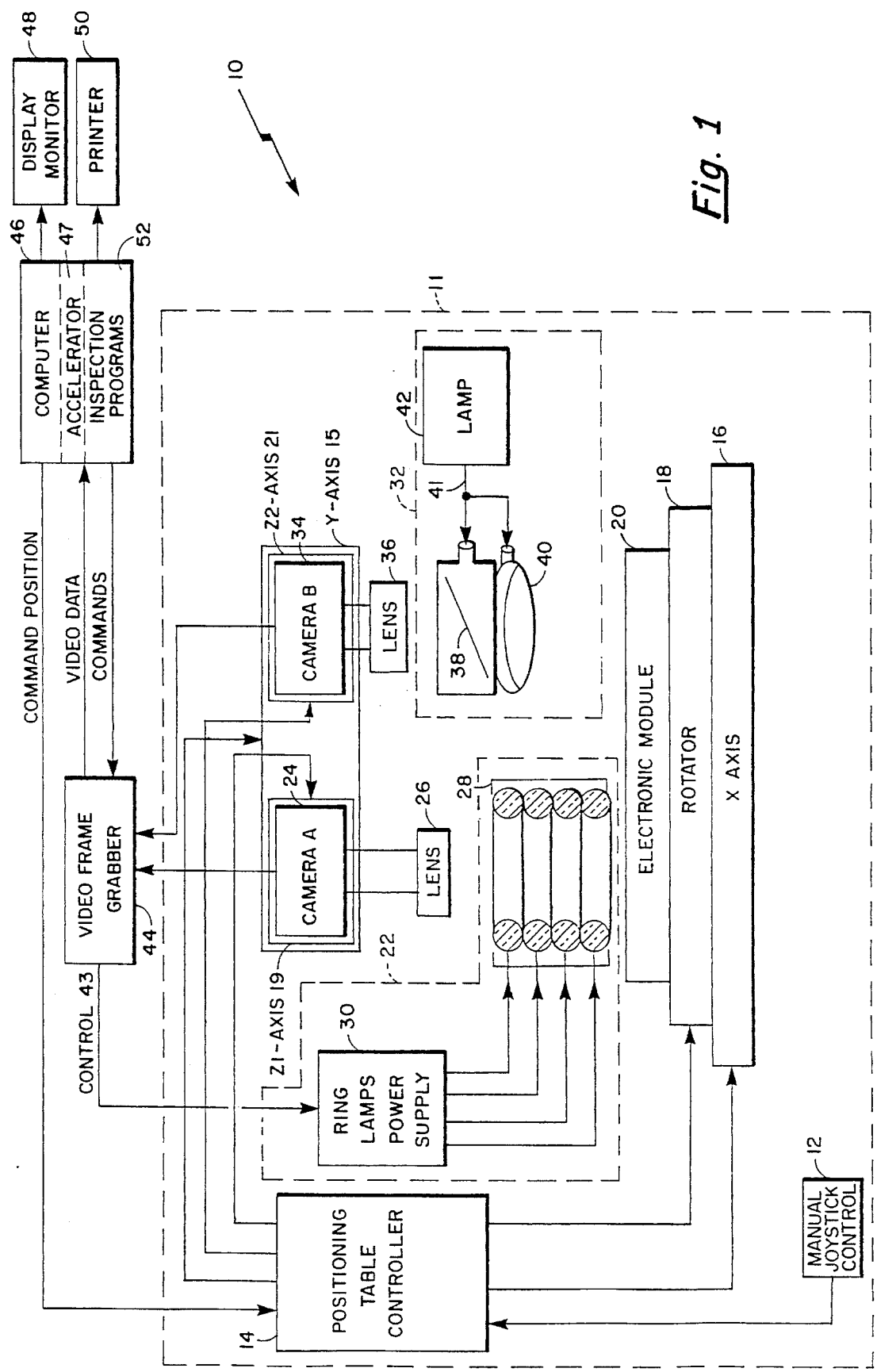
FIG. 1 is a block diagram of an apparatus for automatically inspecting an electronic module.

Referring to FIG. 1 there is shown a block diagram of an automated vision inspection system 10 for inspecting an electronic module 20 to detect defects thereon comprising a five axis positioning table 11, positioning table controller 14, manual joystick control 12, a dark field illumination source 22, a bright field illumination source 32, two solid state two-dimensional array sensor cameras, camera A 24, camera B 34, each coupled to lens 26 and lens 36 respectively, a video frame grabber 44, a computer 46 which includes an accelerator processor 47 and inspection programs 52, and a display monitor 48 and printer 50 coupled to the computer 46. The dark field illumination source 22 and the bright field illumination source 32 illuminate the electronic module 20 to produce visual images, via camera A 24 and camera B 34 and the video frame grabber 44, which are used to identify defects. The positioning table 11 aligns the module under test with the optical axis of first camera A 24 and then camera B 34 thereby enabling the same field-of-view to be observed under different illumination conditions. The lighting associated with the dark field illumination source 22 preferentially illuminates non-flat surfaces but not vertical surfaces. The lighting associated with the bright field illumination source 32 preferentially illuminates relatively flat surfaces. The images are analyzed by the inspection programs 52 in the computer 46 which includes the accelerator processor 47 to determine component, printed circuit board and solder joint defects of the electronic module 20. The electronic module 20 typically comprises a plurality of surface mounted devices (SMD) which include multiple leaded devices, leadless devices and axial leaded devices, and all other such devices that may be soldered to the printed circuit board (which are readily known to one skilled in the art). The devices, soldered connections and printed circuit boards are inspected for defects by the automated vision inspection system 10 by systematically and repeatedly (in order to examine the entire electronic module 20) positioning small portions of the electronic module 20 within the field of view of camera A 24 and camera B 34. With manual joystick control 12, the operator calibrates the axes of electronic module 20 with the axes of the positioning table 11, under the direction and supervision of the computer 46. The post-calibration positioning of the electronic module 20 is conducted automatically via a Command Position signal from the computer 46 to the positioning table controller 14, with respect to a prior chorography entailed within an electronic module PCB data base 129 (FIG. 8A and 8B) which resides in the computer 46. The inspection of the electronic module 20 upon image acquisition from camera A 24, camera B 34, via commands to video frame grabber 44 with transacted video data is performed within the computer 46 and the accelerator processor 47, by the inspection programs 52 which is in accordance with Section 4.4 of MIL-STD-2000A (Standard Requirements for Soldered Electrical and Electronic Assemblies). Table 1 lists those fifteen categories of inspection performed by the inspection system 10 and the manufacturing process variables related and regulated by each inspection category through statistical process control monitors with embedded Markov models.

TABLE 1

| AUTOMATED INSPECTION CATEGORY | MANUFACTURING VARIABLE |
|---|---|
| Good solder connection | All variables within tolerance |
| No component | Error prior to automated soldering process |
| Nonsoldered connection | Volume of solder, pressure of hotbar, contact time between hotbar and solder joint, contact point of hotbar with respect to lead |
| Contaminant | Foreign matter embedded in solder, poor cleaning, excess time-temperature |
| Cold solder | Temperature of hotbar, thermal transfer, contact time between hotbar and solder |
| Overheated solder | Temperature of hotbar, contact time between hotbar and solder, contact point of hotbar with respect to lead |
| Insufficient solder | Volume of solder, pressure of hotbar |
| Excessive solder | Volume of solder |
| Pits, voids, and icicles | Temperature of hotbar, volume of solder |
| Solder bridging | Volume of solder, hotbar departure rate, lead placement |
| Exposed PCB fiber | Error prior to automated soldering process |
| PCB measling, PCB contamination, PCB delamination, and lifted lands | Error prior to automated soldering process, time-temperature of hotbar, or poor cleaning |
| Charred | Temperature of hot bar thermal transfer |
| Lead misplaced, lead disturbed | Lead misplaced, or part moved during solder operation |
| Other defects: Fractured, cracked, non-wetting, dewetting, cracks in conformal coating | Manufacturing variables not directly regulated |

Figure 3A:
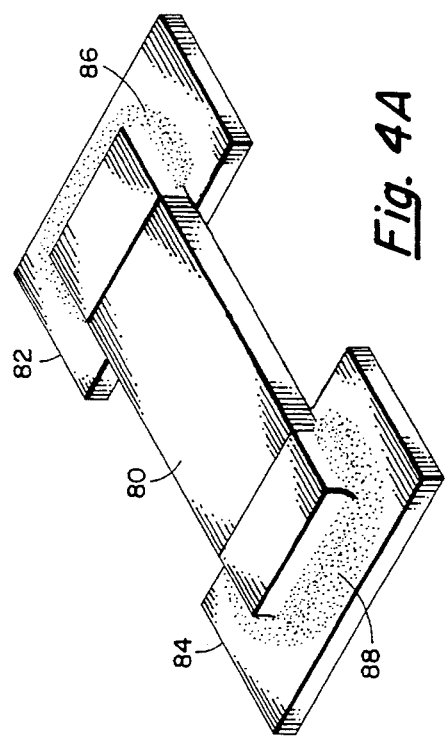
FIG. 3A and FIG. 3B show, respectively, a perspective view and a top view of an enlarged portion of a surface mounted leaded device attached with solder to a solder pad on a printed circuit board.
Figure 3B:
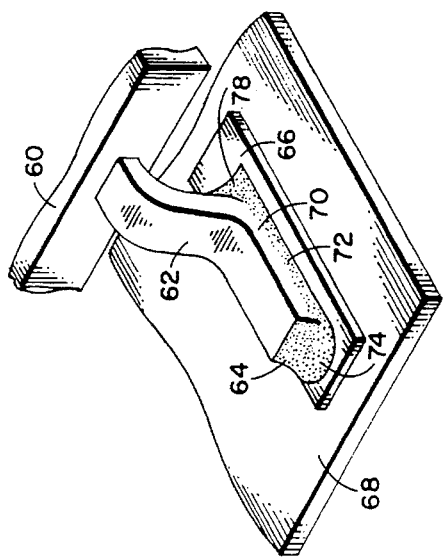

Referring to FIG. 3A and FIG. 3B, FIG. 3A shows a lead 62 from a leaded device 60 attached with solder to a solder pad 66 on a printed circuit board 68. The inspection of the resulting solder joint 64 between the lead 62 and the solder pad 66 is primarily concerned with the side of the foot portion 70 for the lead 62. The foot portion 70 is positioned flat on the solder pad 66 typically requiring only a small amount of solder to make a proper connection. A meniscus solder fillet 72 is disclosed from under the foot 70 to the sides and back of the foot 70. The portion of the meniscus solder fillet 72 to the front of the foot 70 is the toe 74. The portion of the meniscus solder fillet 72 to the rear of the foot 70 is the heel 78. Further assessments of solder joints may be found in MIL-STD-2000A. FIG. 3B shows a top view of lead 62 soldered to solder pad 66.

Figure 4A:
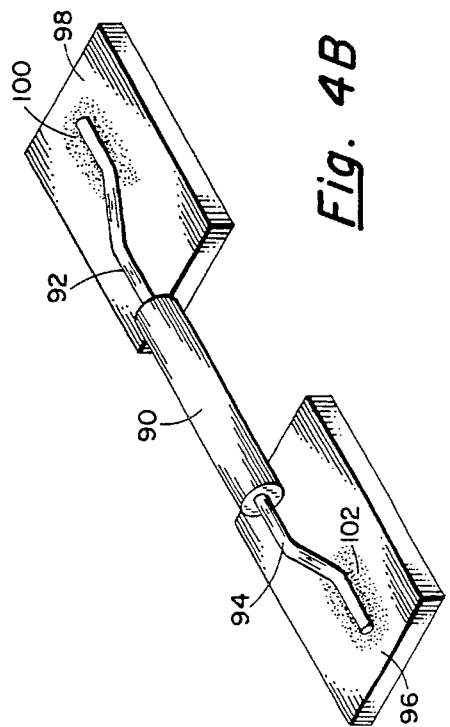
FIG. 4A and FIG. 4B show, respectively, a perspective view of an enlarged portion of a surface mounted leadless device attached with solder to solder pads, and a perspective view of an enlarged axial device attached with solder to solder pads.
Figure 4B:
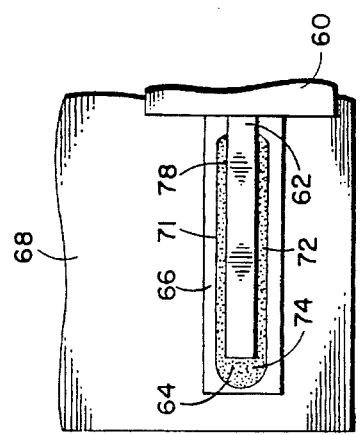

Referring now to FIG. 4A and FIG. 4B, FIG. 4A shows a leadless device 80 having a solder joint 86 at one end where the device 80 meets solder pad 82 and a solder joint 88 at the other end where the device 80 meets solder pad 84. FIG. 4B shows an axial device 90 having two leads 92, 94 wherein lead 92 is soldered to solder pad 98 resulting in a solder joint 100 and lead 94 is soldered to solder pad 96 resulting in a solder joint 102.

Figure 2:
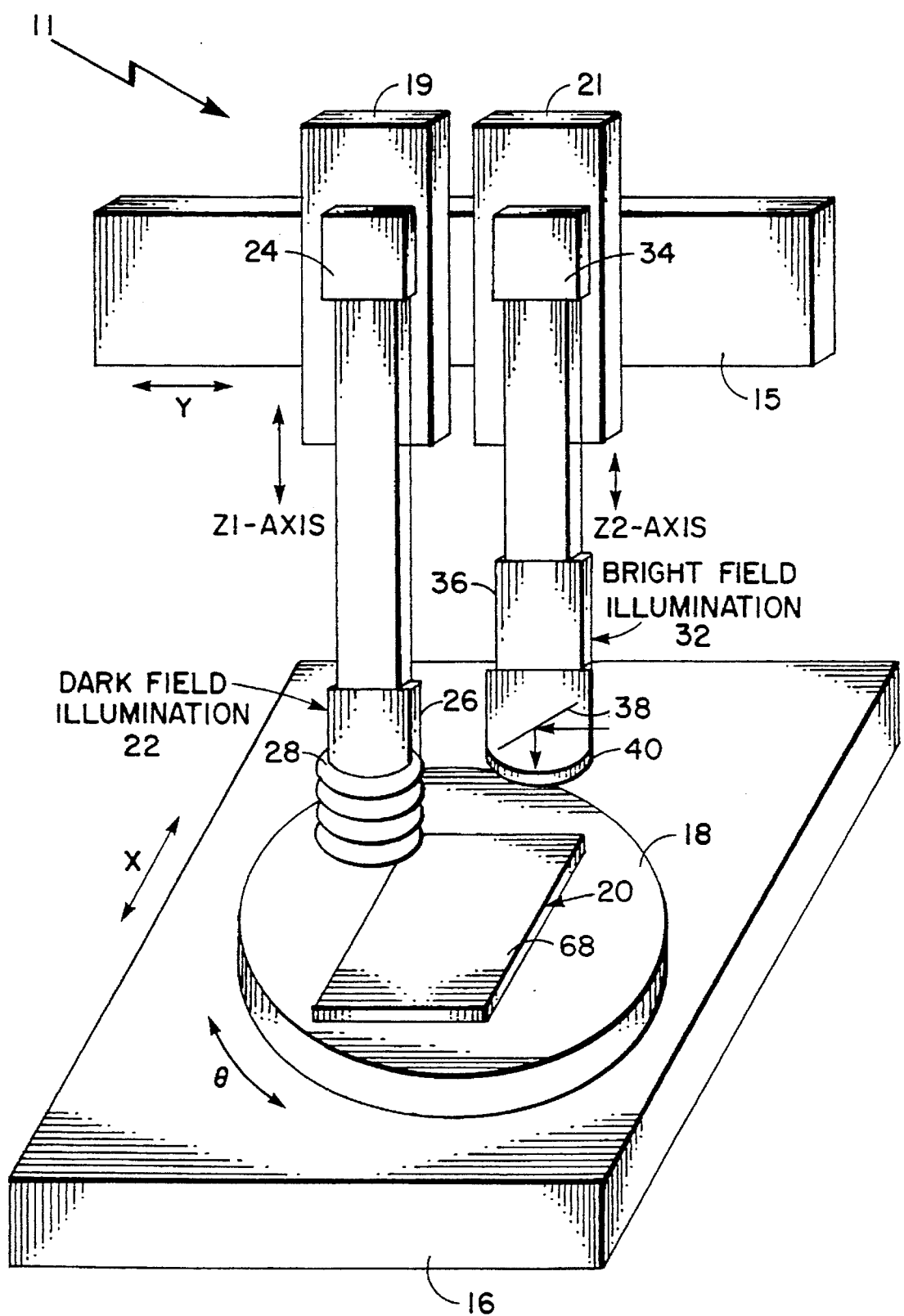
FIG. 2 is a perspective view of a five axis positioning table shown in FIG. 1 having a dark field illumination source and a bright field illumination source positioned along the Z1-axis and Z2-axis.

Referring now to FIG. 1 and FIG. 2, the electronic module 20 typically having a plurality of components such as identified in FIGS. 3A, 3B, 4A and 4B, is mounted to a five axis positioning table 11 comprising a linear X-axis 16 positioning table, a linear Y-axis 15 positioning table, a rotator 18 for theta-axis movement, a linear Z1-axis 19 for positioning the camera A 24 and a linear Z2-axis 21 for positioning the camera B 34 above the inspection plane of the electronic module 20. The X-axis 16 and Y-axis 15 positioning stages enable all components to be positioned into the field of view of camera A 24 and camera B 34. The rotator 18 for theta (θ)-axis positioning is used to align during calibration (a prequisite to automated inspection of electronic module 20) the printed circuit board coordinates with the X-axis 16 and Y-axis 15 coordinates, which in turn are aligned to the camera A 24 and camera B 34 sensor axes. Each camera 24, 34 is focused onto the inspection plane of the electronic module 20 by the Z1-axis 19 and Z2-axis 21 portions of table 11 because the camera lenses have fixed focal length. The precision of camera 24, 34 focus onto the inspection plane of the electronic module 20 is immune to fluctuations of the height of the inspection plane due to the depth of field afforded by the lenses 26, 36. In the present embodiment the position table 11 is manufactured by New England Affiliated Technologies of Lawrence, Mass. The X-axis 16 comprises a 20 inch travel linear air bearing table with a linear brushless servo motor and one micron linear encoder. The Y-axis 15 comprises a 19 inch travel linear air bearing table with a linear brushless servo motor and one micron linear encoder. The Z1-axis 19 and Z2-axis 21 comprise 6 inch travel, Model LM-600-SM, precision grade, cross-roller mount table with a brushless servo coupled to 10 pitch lead screw. The rotator 18 comprises Model RT-12-SM with a 16 arc-second laser rotary encoder. The positioning table controller 14 is Model NEAT 310B with a RS-232 communication interface for each of the five axes. The command and control signals to the positioning table controller 14 originate from the computer 46 which conveys the appropriate signal in order to locate the desired position within the field of view of the camera.

Figure 5:
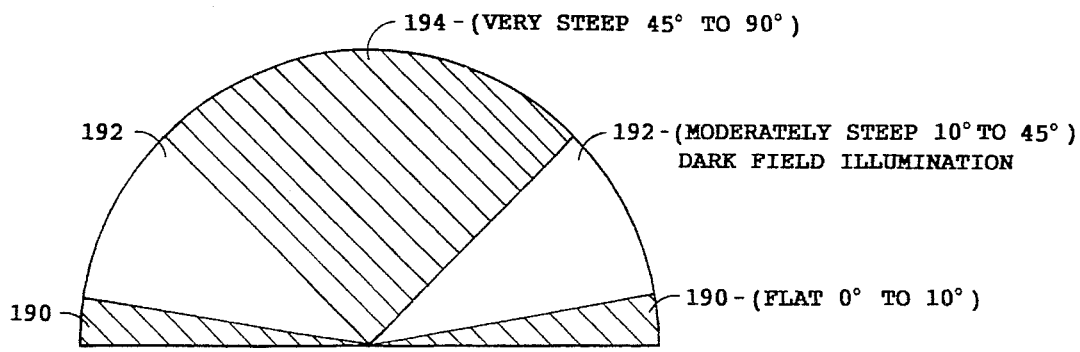
FIG. 5 shows a dark field illumination reflected light pattern when the ring lamps are powered continuously.
Figure 7:
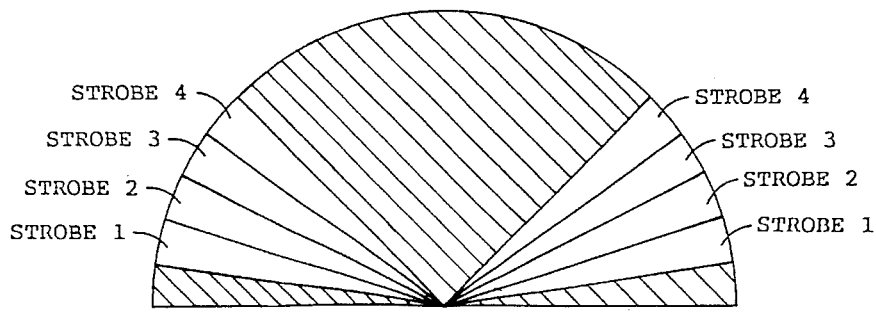
FIG. 7 shows the dark field illumination reflected light pattern when the ring lamps are power strobed separately.

The dark field illumination source 22 is disposed under the solid state two-dimensional array sensor camera A 24 supported by the Z1-axis 19 structural portion of the positioning table 11 (FIG. 2), and the lens 26 is attached to the camera A 24. The dark field illumination source 22 comprises four ring lamps 28 stacked to form a cylinder which are powered by a ring lamps power supply 30 in accordance with a Control signal 43 from the video frame grabber 44. Each of the ring lamps 28 are powered continuously, but they also may be triggered (power strobed) separately by the ring lamp power supply 30 in accordance with the Control signal 43 provided to the ring lamps power supply 30 for applications requiring finer topology resolution. When the ring lamps 28 are powered continuously by the ring lamp power supply 30 constant illumination flux density is maintained from the output of ring lamps 28 because of optical monitoring of the output flux density using a photoresistor sensor (not shown). Such photoresistor sensor forms a feedback circuit to the power supply 30 and regulates the power supplied to the ring lamps 28. The dark field illumination source 22 illuminates surfaces between 10 degrees and 45 degrees when all four ring lamps are powered continuously as shown in FIG. 5 and Table 2 to the parallel plane of the sensor to obtain an image for processing by inspection programs 52. The dark field illuminates surfaces reflectively between 10 degrees and 45 degrees with respect to the power strobed ring lamps 28 as shown in FIG. 7 and Table 3 to obtain images for processing by inspection programs 52.

TABLE 2

| OBJECT SURFACE ANGLE | LIGHT INTENSITY FROM OBJECT | |
|---|---|---|
| | BRIGHT FIELD ILLUMINATION | DARK FIELD ILLUMINATION |
| Flat (0° to 10°) | high | low |
| Moderately steep (10° to 45°) | low | high |
| Very steep (45° to 90°) | low | low |
| Shadow onto moderately steep surface | low | low |
| Shadow onto flat surface | high | low |
| Shadow onto very steep surface | low | low |

TABLE 3

| RING LAMP POWERED | ANGLES ILLUMINATED WITH HIGH INTENSITY |
|---|---|
| Strobe 1 | 36° to 45° |
| Strobe 2 | 27° to 36° |
| Strobe 3 | 18° to 27° |
| Strobe 4 | 10° to 18° |

Figure 6:
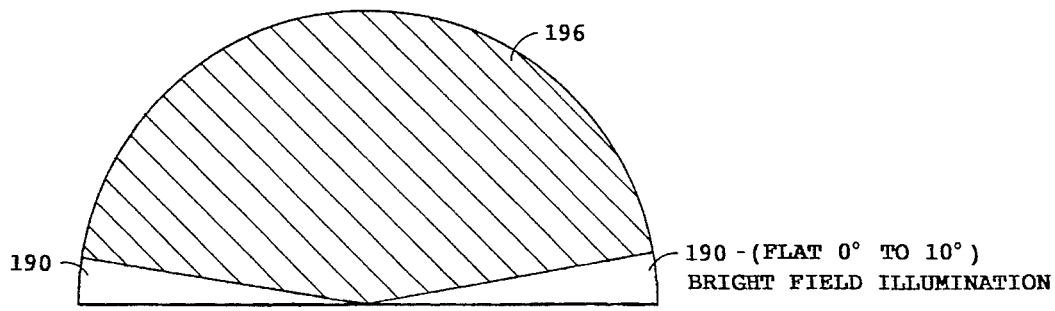
FIG. 6 shows a bright field illumination reflected light pattern.

The bright field illumination source 32 is disposed under the solid state two-dimensional array sensor camera B 34 supported by the Z2-axis 21 structural portion of the positioning table 11 (FIG. 2), and the lens 36 is attached to the camera B 34. The bright field illumination source 32 comprises a lamp 42 which provides light via a fiber optic cable 41 to a partially reflecting mirror 38 mounted in front of the lens 36 and to a miniature fiber optic ring light 40 attached under the partially reflecting mirror 38. The bright field illumination source 32 illuminates surfaces that are close to parallel to the sensor as shown in FIG. 6 and Table 2 (i.e., plus or minus 10 degrees tolerance about the plane parallel to the sensor, which allows for manufacturing variations of solder joints) in order to obtain an image for processing by inspection program 52. The preferred working distance has to be large in order to meet the illumination objective for the bright field, i.e., illuminate flat surfaces. The field of view of both camera A 24 and camera B 34 is made the same at different working distances by the use of zoom lenses. The consequential reduction of light level illuminating the electronic module 20 is accounted for by either increasing the output energy of the lamp 42, by increasing the video gain level of the camera 34 and increasing a dark signal clamp of video frame grabber 44 to proportionately desensitize the apparent increase in dark signal caused by video gain alteration, by accounting for the change in image density by reducing software threshold levels during analysis by the inspection programs 52, or by making a software gain correction per pixel by the inspection programs 52.

In the present embodiment camera A 24 and camera B 34 are embodied by Model TM 640 manufactured by Pulnix America, Inc., of Sunnyvale, Calif. The lenses 26, 36 are embodied by Models 1-6000 (6.5×Zoom), 1-6010 (Coupler), 1.6015 (1× Adapter), 1-6030 (2× Adapter) manufactured by D.O. Industries, of East Rochester, N.Y. The dark field illumination source 22 includes the combination of the ring lamps 28 which are embodied by Model S & Y 9-110 manufactured by Stocker & Yale Inc. of Beverly, Mass., and linear florescent lamps integrated into ring lamps 28 which are embodied by Model BF650 manufactured by JKL Components Corporation of Pacoima, Calif., and ring lamps power supply 30 is embodied by Model FL0664-4, manufactured by Mercron of Richardson, Tex. The collimated light source reflector 38 is embodied by Model D & O Collimated Source manufactured by D.O. Industries of East Rochester, N.Y. The miniature fiber optic ring light 40 is embodied by Model D & O T-Q/AN-3 manufactured by D.O. Industries, Inc., of East Rochester, N.Y. The lamp 42, a halogen light source, is embodied by Model TQ/FOI-1, manufactured by D.O. Industries, Inc., of East Rochester, N.Y.

The video frame grabber 44 receives and digitizes the images obtained by camera A 24 and camera B 34 and transfers such images to the computer 46 via a SCSI (small computer systems interface) bus for processing by the inspection program 52. In the present embodiment, the video frame grabber 44 is embodied by Model DSAM FGM manufactured by Analogic of Peabody, Mass. The computer 46 which includes the display monitor 48 is embodied by Model SPARC STATION 2, 4/75 GT-16-P40, manufactured by Sun Microsystems, of Mountain View, Calif. A computer accelerator incorporated into the computer 46 via a SCSI bus is embodied by Model SKYSTATION, manufactured by Sky Computers, Inc. of Chelmsford, Mass. The color printer interfaced to the computer 46 via SCSI bus is embodied by Model CH5000, manufactured by Seiko Instruments of San Jose, Calif.

Figure 8A:
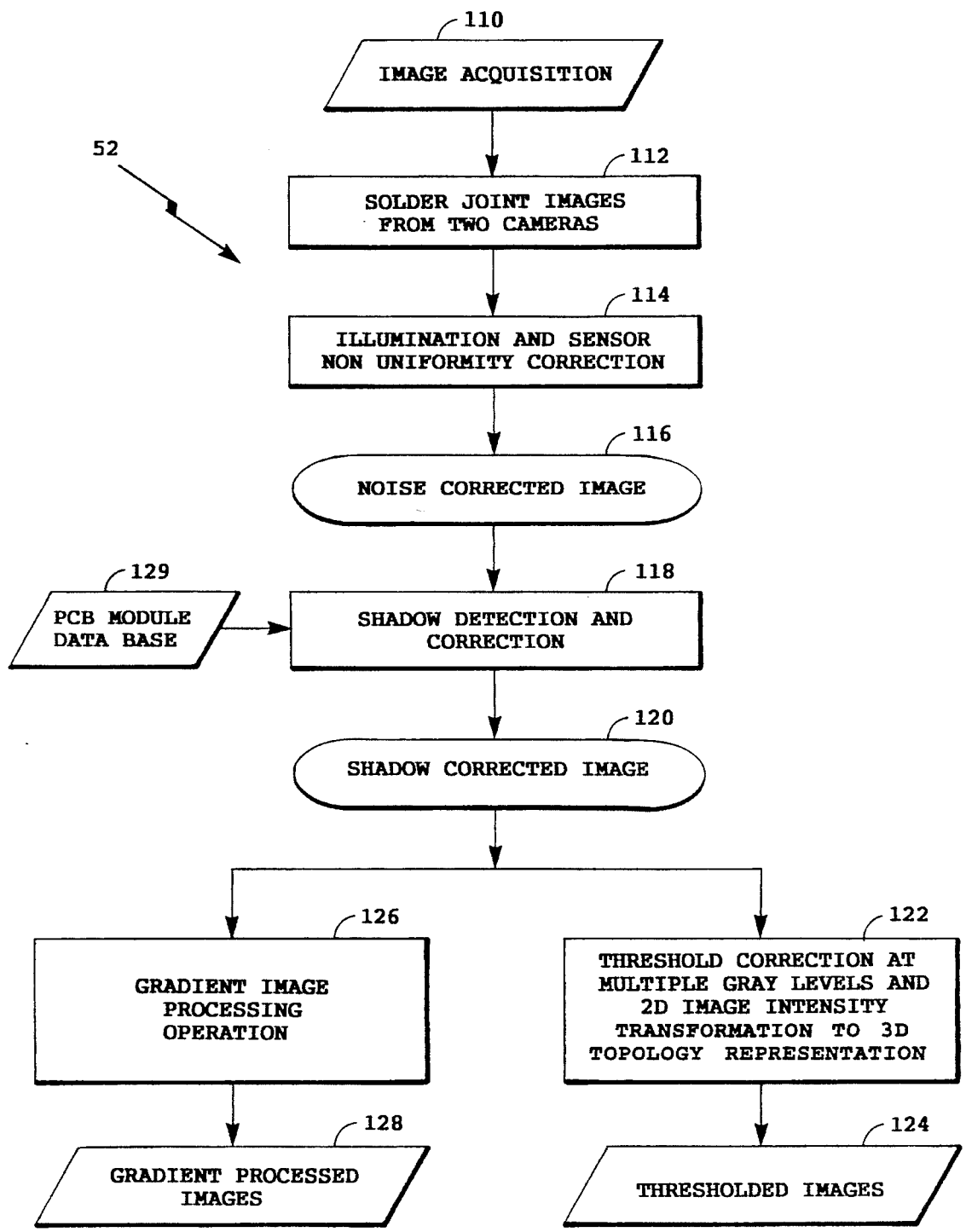
FIG. 8A and FIG. 8B together form a flow chart of an inspection program executed by a computer within the apparatus of FIG. 1.
Figure 8B:
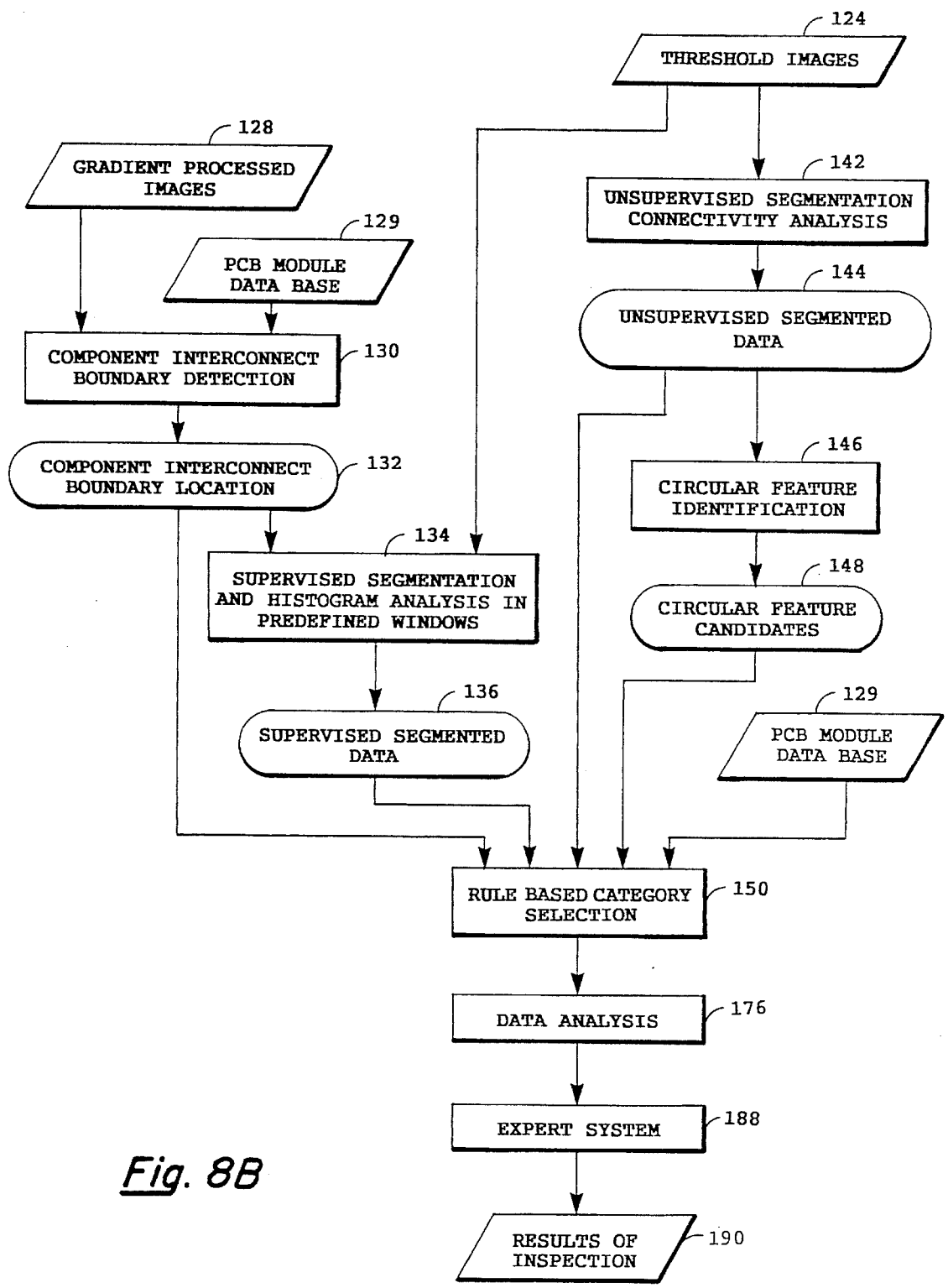

Referring now to FIG. 8A and FIG. 8B, the computer 46 and the accelerator processor 47 execute the inspection programs 52 for processing the images received from the camera A 24 and camera B 34. Following the image acquisition 110 which stores the solder joint images from two cameras 112, (cameras 24, 34) an illumination and camera nonuniformity correction 114 is performed on the images which produces a noise corrected image 116. This step performs fixed pattern noise correction which comprises correction of camera dark signal nonuniformity per pixel evaluated by an ensemble average of images acquired with no illumination, and a correction of the combined camera as well as illumination nonuniformity evaluated by an ensemble average of images taken of a uniform low optical density object. The correction terms are valid because of constant integration time, constant illumination flux density, constant camera temperature and stable electrical characteristics of the inspection system 10. The corrections per image pixel are a subtraction term for each of the pixels within the image to normalize the dark signal nonuniformity contributions, and a multiplication term for each of the pixels within the image to normalize the camera gain as well as illuminating nonuniformity contributions.

Next, a shadow detection and correction 118 operation is performed on the noise corrected image 116 to produce a shadow corrected image 120. Shadows are cast onto the inspection plane of the electronic module 20. The area of the shadow depends upon the height of surface mounted devices (SMD) of the electronic module 20. If SMT devices are located in the area affected by shadow then the expected reflectance of the surface is lowered. If SMT devices of equal height are adjacent to one another, then the shadow will be omni-directional with a uniform reduction of reflectance over the entire field of view of the camera. However, small surface mounted devices in the vicinity of large SMDs will exhibit shadow casts that are unidirectional. A unidirectional shadow cast onto a solder joint will have a pronounced discontinuity of reflected light from a defined area of the joint.

The detection of omni-directional shadows is possible because of the absence of shadows that result from bright field illumination 32. Omni-directional shadows affect only the objects from the dark field illumination 22. A consequential reduction of intensity of images acquired under dark field illumination 22 with omni-directional shadows would result in the inspection programs 52 rejecting the joints under inspection on grounds of low reflectivity surfaces, indicative of temperature abnormalities in the manufacturing process. The conditions that give rise to omni-directional shadows are validated from the information residing under a PCB module data base 129. For a defined field of view of the inspection module 20, the PCB module data base 129 is checked for the proximity of components of equal heights that would alert the inspection programs 52 of the presence of omni-directional shadows. The inspection programs 52 compare the relative difference of reflectivity of the dark field illuminated image and the bright field illuminated image. Since only the dark field illuminated images are affected, the solder reflectivity is lower in comparison to the bright field images. The relative discrepancy of the reflectivity is the magnitude of the omni-directional shadow cast. The dark field image is proportionally corrected by applying a software gain per pixel in the entire field of view. However, if the relative difference in intensity of the dark field image and bright field image is negligible, no gain correction is applied.

The detection of uni-directional shadows is also possible because of the absence of shadows that result from bright field illumination 32. Therefore, a comparison of both dark field and bright field images as shown in Table 2 conveys the presence of a shadow onto a moderately steep surface plane (10 degrees to 45 degrees). The illuminated plane in the region of shadow is of low intensity that would ordinarily be rejected as a discontinuity of intensity profile. If the discontinuity is of a nature indicative of solder crack or hair line contaminant (i.e, narrow region of discontinuity), then the joint is classified as a reject. However, shadow casts in general are of a larger area, and since the knowledge of the proximity of a component of greater height is known (this is established from the PCB module data base 129), a low intensity illuminated surface (penumbra area) onto a region of the solder joint under inspection can be inferred to be of the same neighboring (outside penumbra area) joint profile intensity provided the region is of low intensity in both the dark field and the bright field illuminated images as shown in Table 2.

Still referring to FIG. 8A, the shadow corrected image 120 is checked for uniform intensity spatial distribution within predetermined areas of the solder joint. This is done by the operation of threshold correction at multiple gray levels and 2D image intensity transformation to 3D topology representation 122 which results in thresholded images 124. This step is conducted by thresholding the two-dimensional (2D) gray scale image within regions of gray scale intensity values. The image is transformed to a binary representation (1 if intensity is within defined 2D gray scale intensity range, and 0 if intensity is not within defined 2D gray scale intensity range) for ease of analysis. Within a 2D gray scale intensity range the information conveyed is the three-dimensional (3D) angle of the surface (surface normal to incident illumination and reflected illumination), and this forms the basis of transposition from 2D intensity to 3D topology descriptions, the reflectivity of the surface (threshold 2D gray scale intensity range), and the spatial distribution of the angle and reflective surface. Three gray scale threshold intensity ranges equally spaced over the 2D image gray scale are used and found to be adequate in deciding if a joint is defective. In some applications, the inclusion of further 2D gray scale intensity ranges may be necessary for accurate determination of solder joint defect category. Since 3D surface angle resolution is a function of the incident illumination angle, in order to resolve surface angles between the ranges of 10 degrees to 45 degrees as shown in FIG. 7 and Table 3, it is necessary to power strobe the ring lamps 28 in succession. An image must be acquired for each angular incident illumination that results through power strobing. The present preferred embodiment does not power strobe the ring lamps 28. It was determined that adequate information is conveyed by modeling the solder joints as flat (0° to 10°), moderately steep (10° to 45°), and very steep (45° to 90°) areas. Therefore, in the present embodiment angular surface between 10 degrees and 45 degrees all represent one angle plane in the inspection programs 52. The 3D slope of the solder fillet is determined by the width of the 2D binary image representation of the thresholded high intensity points. The width of the high intensity points from the edge of the device interconnection boundary is linearly interpolated (first order interpolation) to measure the 3D slope of the solder fillet, and thus a 3D contact angle between the solder fillet and solder pad, as well as the 3D angle between the solder fillet and the device interconnection are evaluated. The occurrence of excess solder and cold solder joint defects, which are characterized as a convex solder fillet, are determined by image feature attributes of the Joint types. Excess solder joints resemble a hemispherical topology attribute. Excess solder joints do not exhibit a discernible interconnect boundary, and the spread of binary thresholded data is extensive for dark field illuminated images with little visible flat surfaces when analyzed under bright field illuminated conditions. Cold solder joints have an abrupt angular transition between the solder pad and the solder fillet. The cold joint fillet equally has a hemispherical profile. The fillet is very steep and thus observed as a low intensity area of both dark and bright field illuminated images. These areas are not confused as shadows because of the extent of the fillet displaying the cold fillet region and because the conditions that give rise to the presence of shadows are predicted from the chorography of the PCB module data base 129.

Still referring to FIG. 8A, the shadow corrected image 120 also has a gradient image processing operation 126 performed on it resulting in gradient processed images 128. For the detection of edges within an image such as straight lines formed by a component outline, the present embodiment uses classical image processing gradient detection algorithms (Sobel operator performed on shadow corrected image 120) embodying a global operator performed with the original gray scale image. The image processing gradient detection algorithms are known to one skilled in the art and described in "Digital Image Processing" by William K. Pratt, John Wiley and Sons, Inc., second edition, 1991.

Referring now to FIG. 8B, the gradient processed images 128 and the PCB module data base 129 are forwarded to a component interconnect boundary detection 130 operation which generates a component interconnect boundary location 132; here a template matching operator attempts to fit a best spatial location to an object of known dimension. This technique is used to locate the component interconnect boundary location 132. Since leadless components and leaded components are manufactured to a known tolerance, then knowledge of the orientation of the component and the dimension of the component is sufficient to form the basis of a template (i.e. a theoretical estimate of the feature size). The perimeter of the template region is highlighted by the gradient processed images 128, thus the dimensionality of the perimeter of the template is used in a two-dimensional manner in order to extract the most likely candidate for the component interconnect boundary location 132. The interconnect boundary location 132 is forwarded to both the supervised segmentation and histogram analysis in predefined windows 134 and the rule based category selection 150.

Still referring to FIG. 8B, the component interconnect boundary location 132 is used together with the thresholded images 124 which are then operated on by supervised segmentation and histogram analysis in predefined windows 134 to produce supervised segmented data 136. Supervised segmentation is that process of software defined areas predetermined with respect to solder pad, component interconnect boundary, and solder volume) and the mathematical description of the areas. The solder pad dimensions are known from the PCB module data base 129 for each type of electronic module 20 that is to be inspected, the solder volume per solder pad is known from the PCB module data base 129 and is based on the deposition of solder paste onto the solder pad by a dispenser during the manufacturing process of the electronic module 20, and finally, the component interconnect boundary is evaluated during the inspection via the component interconnect boundary location 132.

Referring now to FIGS. 3A, 3B and 8B, the solder pad 66 and the component interconnect boundary location 132 (an outline of the lead 62) collectively represent a line drawing of the solder joint. This information is sufficient to determine the correct placement of the component 60 onto the solder pad 66. If the component 60 is misplaced onto the solder pad 66, then the component interconnect boundary location 132 will extrude the location of the solder pad 66, and if the component 60 is correctly placed, then the component interconnect boundary region 132 will be located within the solder pad 66; location of the solder pad 66 is known from the PCB module data base 129. Between the component interconnect boundary location 132 and the solder pad 66 is the solder interconnect region 64, i.e., that area where the solder wets to the surface of the solder pad 66 and the component lead 62. The top surface of the component lead 62 under normal circumstances, for good solder joints, should be visible with uniform intensity (indicative of solder wetting without imperfections such as voids, icicles, cracks, solder balls) and orthogonal to the lens of the camera (indicative of the coplanarity of the component to the solder pad; if the component is not orthogonal to the camera then the dimension of the component interconnect boundary will be evaluated to be smaller than the expected dimension residing in the PCB module data base 129). The five major areas of interest, to determine the wetting properties of the solder joint 64, are the right side 71, left side 72, far end 74, and lower end 78 with respect to the component lead 62 and on the top surface of the component lead 62 which is bounded by the interconnect boundary location 132. Each of these five areas are defined as a supervised segmentation window.

Within each of the five windows a mathematical analysis is performed that describes the reflectance of the solder, it's area, and it's continuity. The purpose of the analysis within each window will be to indicate the nature of the solder fillet; the expectation for good solder joints is to observe high reflectance that is smooth and continuous, and the high reflectance must occupy a significant portion of the window. If there is an absence of high reflectance the solder fillet is missing and the joint is classified as unsoldered. If there is an insufficient area of high reflectance, in any of the five windows, the solder joint is classified as having insufficient solder. Within each window or area of interest, column and row histogram of the intensity (high reflectance) is calculated. The calculation simply comprises counting the number of image pixels from camera A24 and camera B34 that exceed a specified threshold with respect to each column and row of a window. Each column within a window is one pixel wide times the width of the window. The histogram within each window will indicate the intensity distribution along the length and width of the window. This process is called supervised segmentation because the areas of interest (the five windows) are predefined with respect to the solder pad 66 and the component interconnect boundary location 132. Depending upon the location of the component interconnect boundary location 132, the software will supervise the segmentation into predefined windows and then conduct the histogram analysis. The dimensions of each window therefore are variable per solder joint and depend on the component interconnect boundary location 132. In comparing the results of the data between solder joints, one could normalize the data and compare the normalized data to one set of parameters within an expert system, or alternatively, normalization can be avoided if the data is compared with respect to a pertinent set of data within an expert system where the set for comparison depends on the component interconnect boundary location 132. The later method requires a larger number of data sets to be stored into the expert system data base. The supervised segmentation and histogram analysis in predefined windows 134 is an efficient descriptor of the solder joint features, except for a few feature types that require two-dimensional descriptors, and these are circular features. Using two one-dimensional descriptors, column intensity and row intensity, of the solder joint fillet within a window as defined by supervised segmentation and histogram analysis within predefined windows 134, it is difficult to describe circular features. The supervised segmented data 136 is forwarded to the rule based category selection 150.

Still referring to FIG. 8B, in parallel with supervised segmented data 136, the thresholded images 124 are forwarded to an unsupervised segmentation connectivity analysis 142 operation. The binary image information is described mathematically by conducting a connectivity analysis. This process groups (labels) all points of the image into mutually inclusive objects. Inclusive points of the image are those that are interconnected by neighboring points of the same intensity value. An object is defined as that region whose perimeter is a transition of intensity ranges. This process of labeling of objects results in a finite number of objects. Each object is characterized by its spatial location, its perimeter, its area, its compactness, its length and width, the number of objects bound by the object (the number of objects within the object), and the proximity of the object to other objects. The object connectivity data is used to evaluate the conformity of solder fillets, the presence of contaminants, measure of texture of joint (excessively rough surfaces are characterized by an increased density of object labels within a region, where in general the objects are highly compact in nature). The results of unsupervised segmented data 144 are forwarded to the rule based category selection 150 and to circular feature identification 146. Highly compact objects as established by unsupervised segmented data 144 are characteristic of a circular feature, and circular features are representative of solder defects such as pits, voids, and icicles. The circular feature identification 146 checks object candidates for circular features that are within a predefined size determined by the user to be representative of a defect. The resulting circular feature candidates 148 are forward to the rule based category selection 150 operation.

Figure 15:
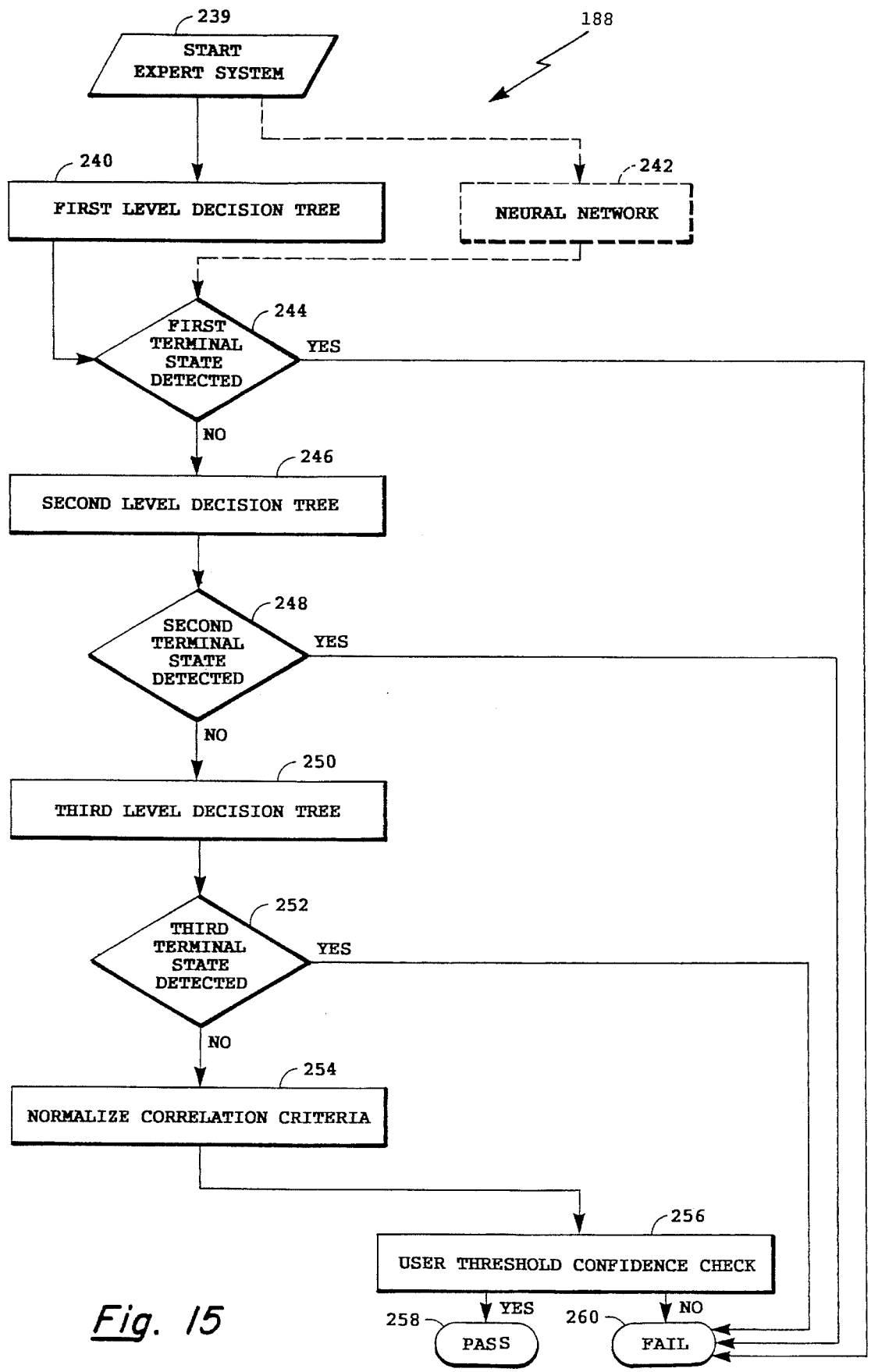
FIG. 15 is a flow chart of an expert system as shown in FIG. 8B and FIG. 14.

Each device used on an electronic module 20 has a defined component size and tolerance. In addition, each type of device has predefined inspection criteria for inspection as specified in MIL-STD-2000A. The rule based category selection 150 comprise a plurality of sets of rules for the various devices on a printed circuit board 68 (FIG. 3A) of electronic module 20 including the printed circuit board 68 itself and such devices may include not only semiconductor devices, capacitors, and resistors, but also connectors. The output from the rule based category selection 150 is forwarded to the data analysis 176. Data analysis 176 comprises a plurality of sets of analysis of the various feature attributes of solder joints and the printed circuit board. The output from the data analysis 176 is forwarded to an expert system 188. The expert system 188 comprises a plurality of sets of decision levels for the results of data analysis 176. The output from the expert system 188 produces the results of inspection 190 indicating a pass 258 or fail 260 (FIG. 15).

Figure 9:
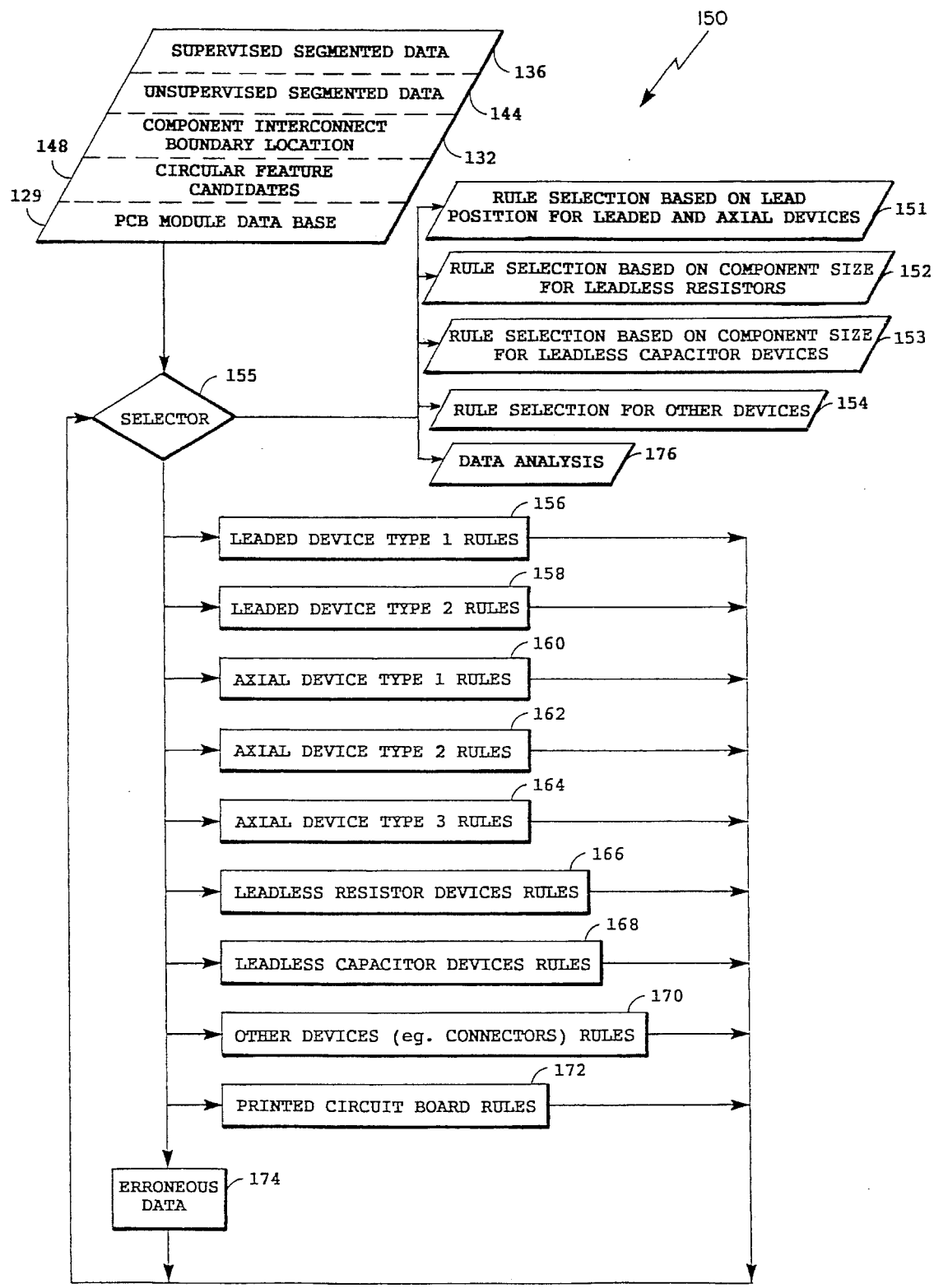
FIG. 9 is a flow chart of a rule based category selection routine shown in the flow chart of FIG. 8B.

Referring now to FIG. 9, a flow chart for the rule based category selection 150 is shown. The five data inputs are the supervised segmented data 136, the unsupervised segmented data 144, the component interconnect boundary location 132, circular feature candidates 148, and the PCB module data base 129. A selector 155 forwards the data to any one of sets of rules 156–172 for the particular device or printed circuit board 68 under test. If the input data are not pertinent to the set of rules, then the data is declared as erroneous data 174 which is identified and conveyed to an inspection system 10 operator.

The printed circuit board rules 172 are the only set amongst the sets of rules 156–172 that do not have hierarchy of rule selection. The present embodiment performs inspection on electronic modules 20 that are void of any markings (letterings that indicate symbolically the reference of the device to the circuit diagram); therefore, the printed circuit board plane is of uniform optical density (constant reflectivity) which is checked by the inspection system 10. The surface reflectivity of the printed circuit board 68 is a function of both the top layer and the inner layer printed circuit board tracks of a multilayer printed circuit board. The location of the printed circuit board tracks are defined within the PCB module data base 129 and used as a template by the inspection programs 52 in order to correlate their presence in the supervised segmented data 136 and unsupervised segmented data 144 of the images acquired by the cameras 24, 34. Within predefined areas dictated by the printed circuit board tracks the printed circuit board 68 is examined for surface reflectance uniformity which is indicative of a normal no-defect situation. The presence of foreign material on the printed circuit board 68 will exhibit a contrast difference that is detected as an increase or decrease in reflectivity; increase in reflectivity is caused by solder splash (including bridging), oxides, measling, exposed fibers, delamination, and decrease in reflectivity is caused by charring, or blistering of the board. The location of all non-uniformities found by the inspection system 10 is conveyed to the user upon completion of electronic module 20 inspection. A further feature of the inspection system 10 is its capability to check for the dimensional conformity of the printed circuit board tracks because of the template matching operation performed to check for printed circuit board 68 defects. Dimensional non-conformity of the printed circuit board tracks is detected as a defect because of the change of reflectivity to that expected. The inspection system 10 can be used to check a printed circuit board 68 with markings provided such markings are spatially and dimensionally identified within a PCB module data base, or alternatively a character recognition subsystem, such as Model 3400 manufactured by Cognex Corporation of Needham, Mass., incorporated into the inspection system 10 would identify the man made markings onto a printed circuit board 68 so as not to confuse them as defect locations. Selection of printed circuit board rules 172 is forwarded to data analysis 176 (FIG. 8B) where reflectance analysis is conducted.

Still referring to FIG. 9, each device used on electronic module 20 has a defined component type, size and tolerance. In addition, as previously pointed out each type of device has predefined inspection criteria for inspection as specified by MIL-STD-2000A. The definitions form multiple unique sets of rules 156–170 that are compared mathematically by the computer 46 and the accelerator processor 47. Also, the volume of solder 64 deposited onto a solder pad 66 (FIG. 3B) is a constant and determined for device interconnection boundary located centrally within the confinements of the solder pad 66. When a device is not positioned centrally with respect to the pad, the topological features of the solder fillet will be different. In order to accommodate for this situation, a further subset of rules that define the decision making process for data analysis 176 (FIG. 14) and the expert system 188 (FIG. 15) are rule selection based on lead position for leaded and axial devices 151, rule selection based on component size for leadless resistors 152, rule selection based on component size for leadless capacitor devices 153 and rule selection for other devices 154.

Figure 10:
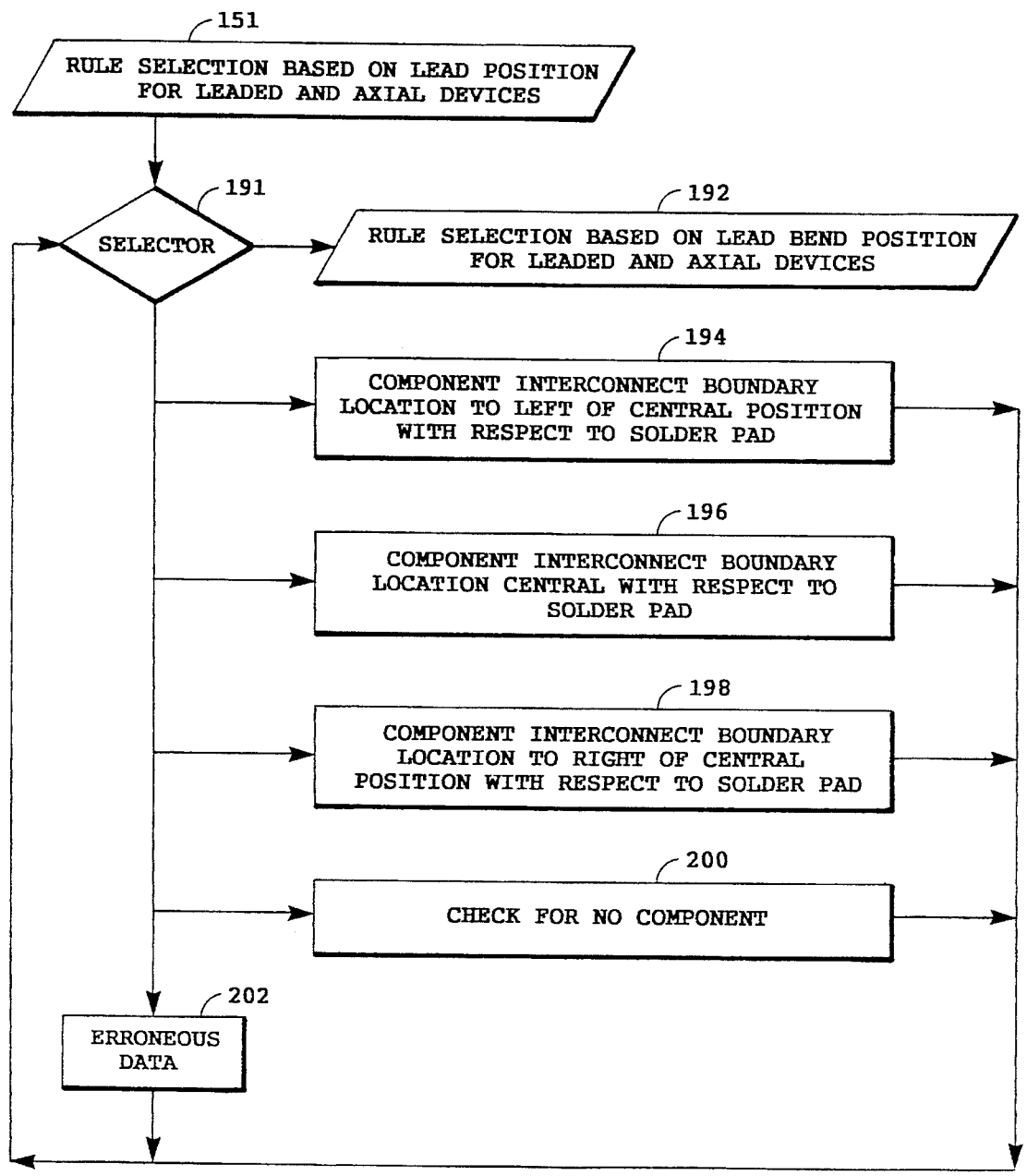
FIG. 10 is a flow chart of a rule selection based on lead position for leaded and axial devices as shown in FIG. 9.

Referring to FIG. 10, rule selection based on lead position for leaded and axial devices 151 has in the present embodiment three unique subsets of rules which reflect a specific position of the device interconnection relative to the solder pad 66 (FIG. 3A). They are component interconnect boundary location to left of central position with respect to solder pad 194, component interconnect boundary location central with respect to solder pad 196, component interconnect boundary location to right of central position with respect to solder pad 198. An additional rule subset, i.e., check for no component 200, is present for situations that require the validation of no component when conveyed by the PCB module data base 129. Check for no component 200 not only validates the absence of a device but also inspects for particular defects such as bridging, icicles, and contaminants. The erroneous data 202 is a trap for inconsistent data. Following the selector 191 selecting a subset of rules, the execution proceeds to the rule selection based on lead bend position for leaded and axial devices 192.

Figure 11:
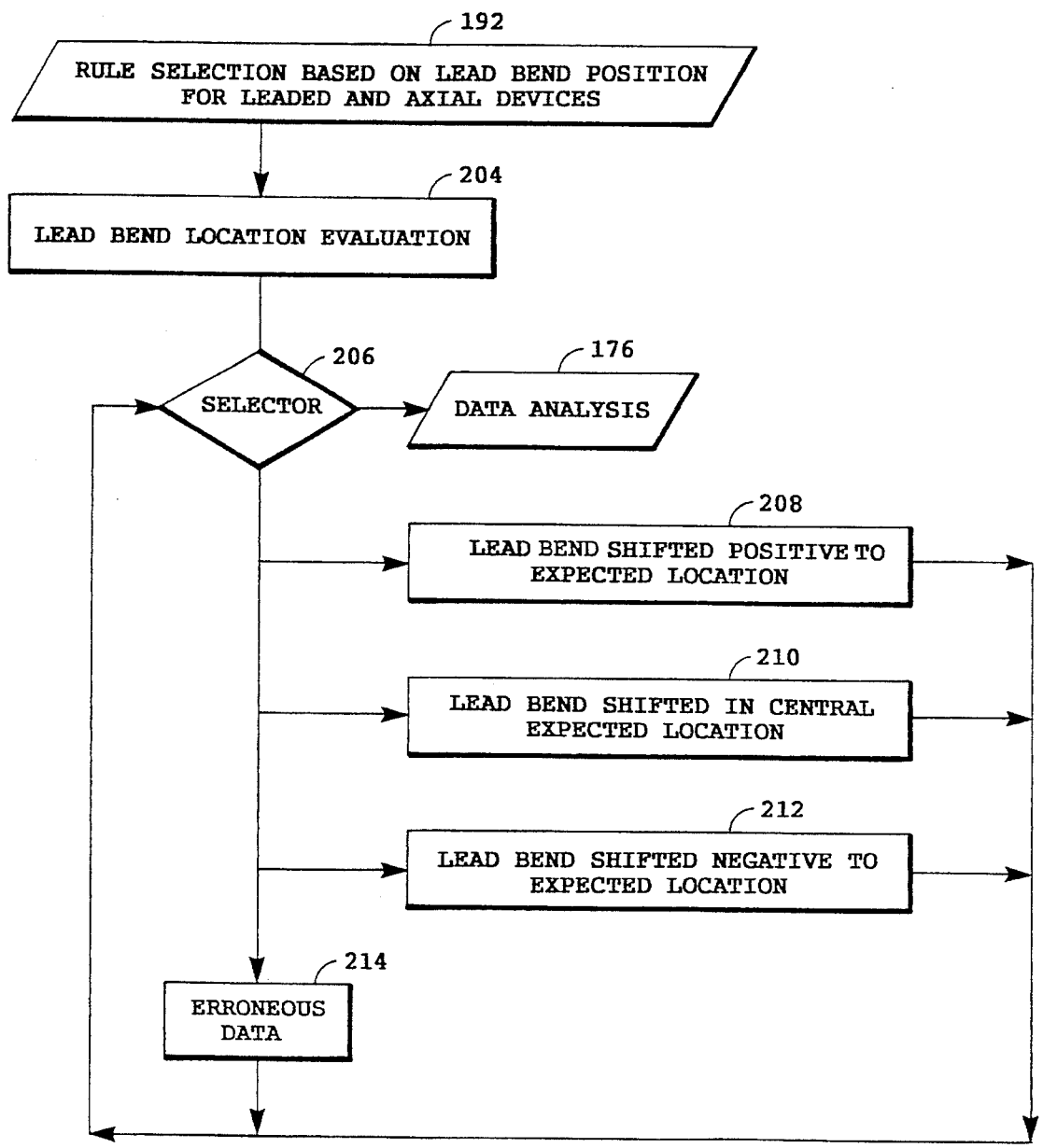
FIG. 11 is a flow chart of a rule selection based on lead bend position for leaded and axial devices as shown in FIG. 10.

Referring now to FIG. 11, upon entering the rule selection based on lead bend position for leaded and axial devices 192 the data is first forwarded to lead bend location evaluation 204. Lead bend location evaluation 204 searches for the lead bend of devices by examining the topology data that should reveal a very steep angle that corresponds to the bend feature. The bend is formed to known dimensions, and therefore the bend will exhibit predictable features to the inspection system 10. When a lead bend location is found, the selector 206 forwards execution to one of three subset of rules comprising lead bend shifted positive to expected location 208, lead bend shifted in central expected location 210, and lead bend shifted negative to expected location 212 which are unique depending on the location of the lead bend relative to the solder pad. Upon completion the selector 206 proceeds to the data analysis 176 routine. If inconsistent data is present, then the erroneous data 214 is selected, and the routine proceeds via the selector 206 to the data analysis 176.

Figure 12:
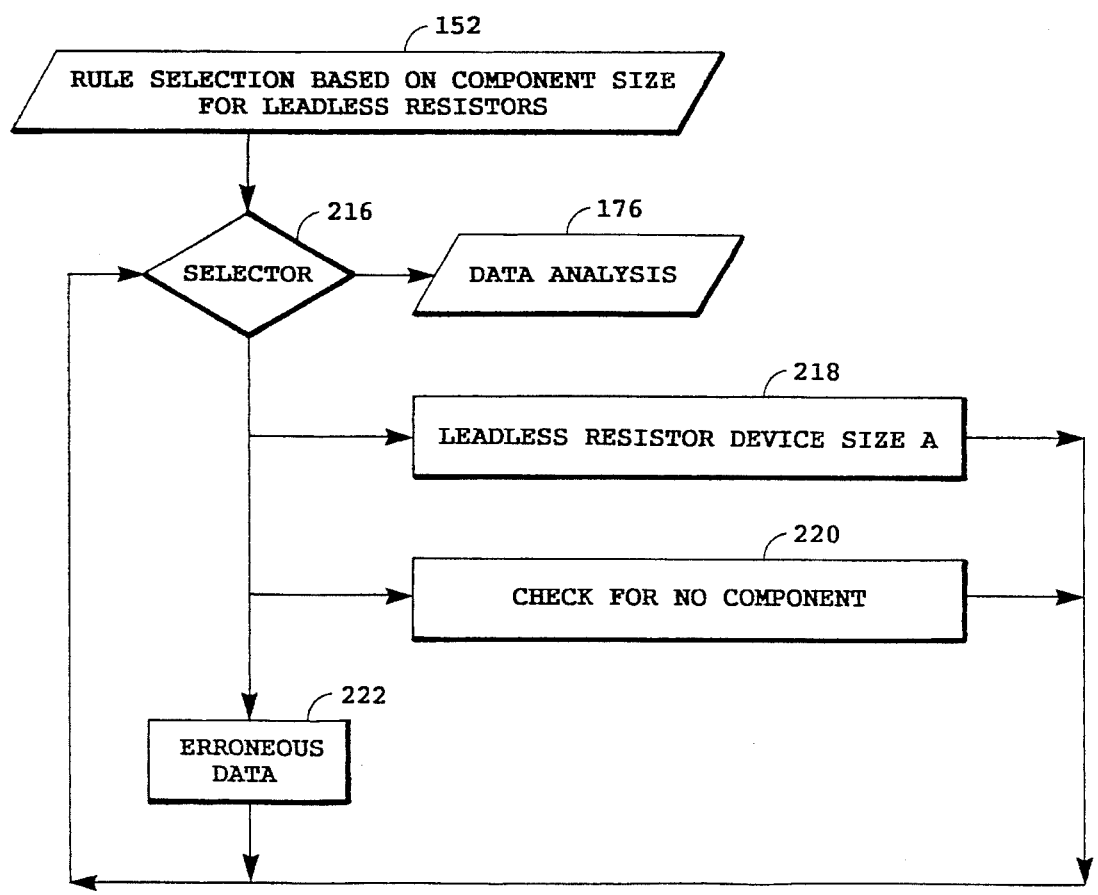
FIG. 12 is a flow chart of a rule selection based on component size for leadless resistors as shown in FIG. 9.

Referring now to FIG. 12, when rule selection based on component size for leadless resistors 152 is selected from the previous selection procedure (FIG. 9) the data within the present embodiment is forwarded by the selector 216 to leadless resistor device size A 218 as this is the only size used in the present electronic module 20. If a no component is declared then the selector 216 forwards the data to check for no component 220. If inconsistent data is found then the erroneous data 222 is selected. Upon selection of a subset of rules the execution proceeds to data analysis 176.

Figure 13:
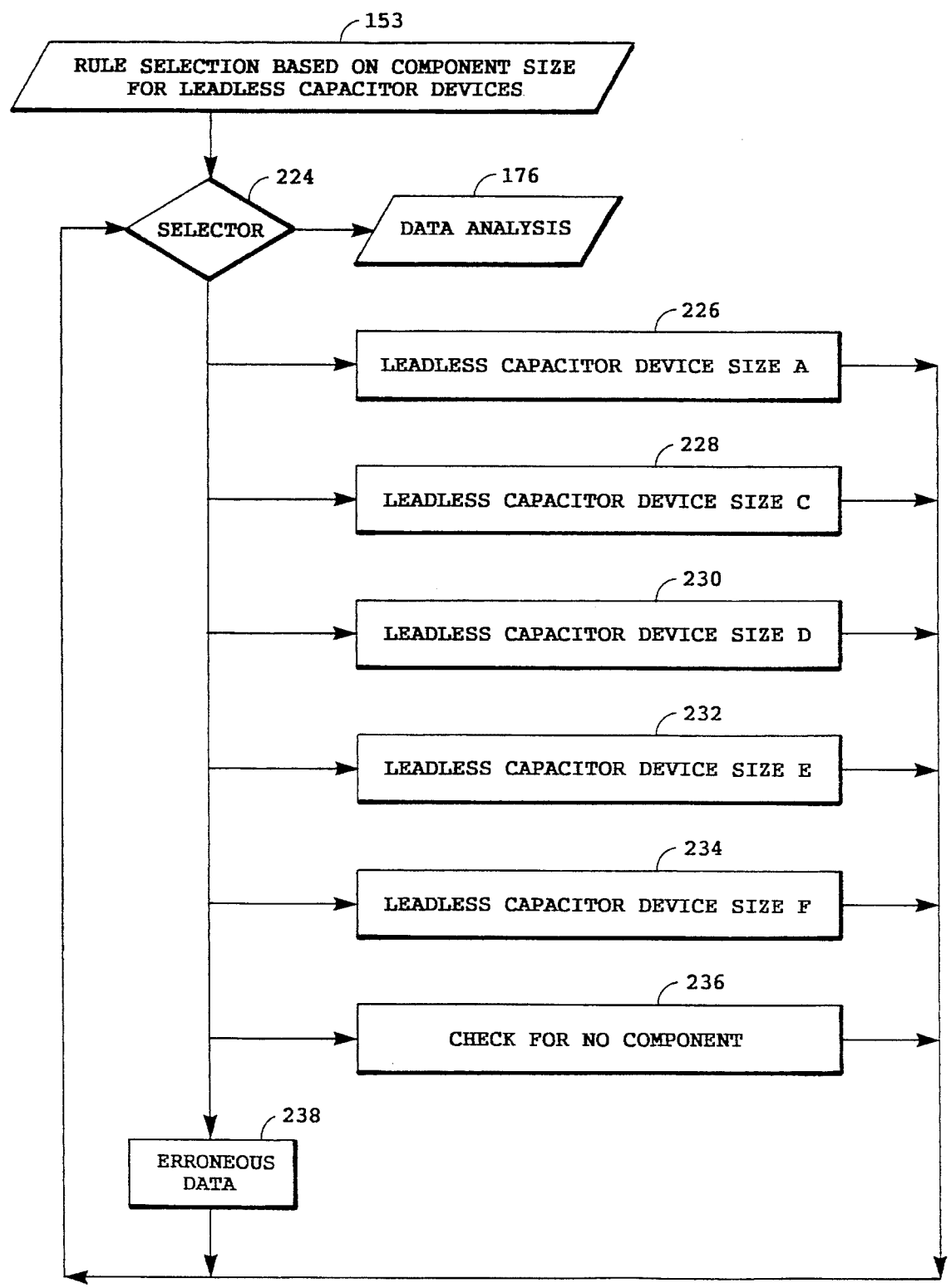
FIG. 13 is a flow chart of rule selection based on component size for leadless capacitor device as shown in FIG. 9.

Referring now to FIG. 13, when rule selection based on component size for leadless capacitor device 153 is selected from the previous selection procedure (FIG. 9), a further selection of subset of rules occurs based on the size of the device by the selector 224. The present embodiment has five size related subset of rules 226–234 that are relevant to the capacitor sizes that can be encountered on the electronic module 20. A further subset of rules, check for no component 236, is selected by the selector 224 when this condition is declared. If inconsistent data is encountered, the erroneous data 238 is selected. Upon completion of the subset of rules selected, the execution proceeds to data analysis 176.

Figure 14:
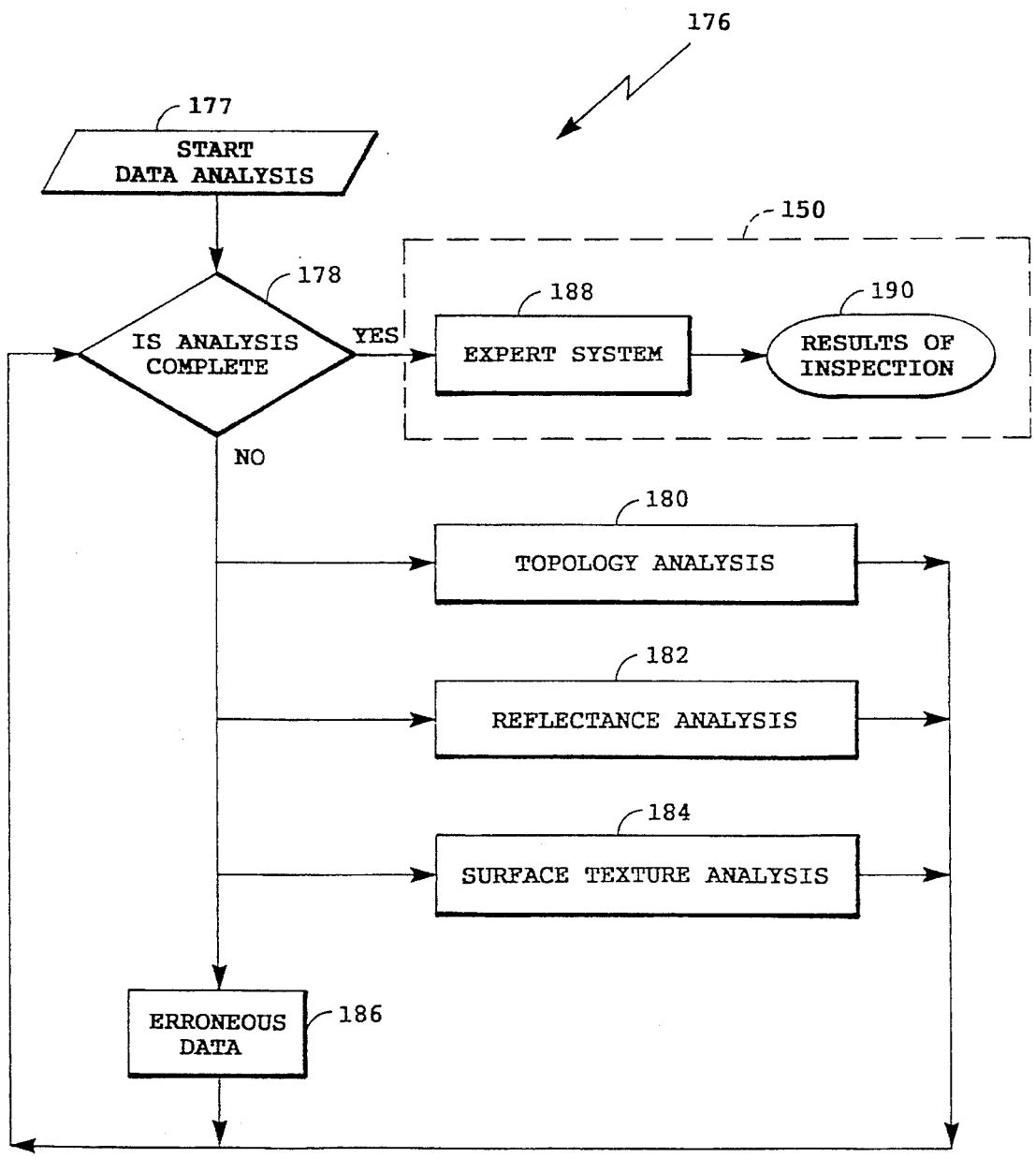
FIG. 14 is a flow chart of a data analysis routine for each of the rules selected in the flow chart of FIG. 9.

Referring now to FIG. 14, a flow chart of the data analysis 176 functions performed is shown comprising a topology analysis 180, a reflectance analysis 182 and a surface texture analysis 184. Each rule subset has a set of preferred parameters that describe the joint under inspection. The parameters within a rule subset pertain to the dimensions of the component, the expected volume of solder, the topology of the joint, the surface reflectivity of the solder and printed circuit board, and the textural surface properties of the joint. The parameters are analyzed as the combined information content of the images, namely the topology and reflectance. Textural information is conveyed by the topology data extracted. Erroneous data 186 is a path for inconsistent information. The topology analysis 180 primarily performs an analysis of surface angles that must be between 10 degrees and 45 degrees adjacent to the device interconnect boundary, representing a solder fillet. The reflectance analysis 182 comprises examining solder fillets for specific reflectivity because specific reflectivity ranges are an indicator of good solder for each specific process. Typically, a highly specular solder joint surface is an indicator of good solder. The surface textural analysis 184 checks for the textural content of solder joints. A good solder joint has smooth surfaces. Texture is indicative of temperature nonconformities or motion between surfaces being joined in the manufacturing process. Texture information is inherent in the connectivity process conducted upon thresholding an image. An abundance of objects found through connectivity analysis is indicative of a rough surface texture; this condition is not representative of good solder joints. Also, an isolated circular texture is indicative of an icicle, void, contaminant, or pit type defects of a solder joint.

Still referring to FIG. 14, when the topology analysis 180, reflectance analysis 182 and surface texture analysis 184 are completed the results are forwarded to an expert system 188. During the comparison of rules performed in the data analysis 176 operation, a set of correlation criteria are established for each parameter defined. A close correlation is sought indicative of a perfect match to the predetermined expected value of that parameter defined by the user. The set of correlation parameters are examined in unison within the expert system 188. The expert system 188 analysis conveys a confidence measure of the results of inspection of the solder joint. The confidence measure is user selected as a criteria for a pass or fail decision which is the result of inspection 190.

Referring now to FIG. 15, the expert system 188 analysis conveys a confidence measure that is directly proportional to the sum total correlation criteria and this measure forms the basis for an affirmative result of pass 258 or fail 260. The vigilance of the inspection process is controlled by the user represented as a user threshold confidence check 256. A high value set by the user for the user threshold confidence check 256 corresponds to joints being classified as pass 258 (i.e. good joints) only when the correlation criteria are closely matched to the user defined theoretical values. An optima of user threshold confidence check 256 will depend on the conformity of the manufacturing process being sought. Each pass 258 or fail 260 result is accompanied with a normalized correlation measure 254 which serves to monitor the manufacturing variables (listed in Table 1) under control, and provided the process is under control, a stable region of the process can be established to reflect an optima for the user confidence threshold check 256 so as to maximize the accuracy of pass 258 and fail 260 results.

Still referring to FIG. 15, the expert system 188 comprises a set of guidelines that represent a hierarchy of precedence of feature attributes. The expert system 188 comprises a first level decision tree 240, second level decision tree 246, and the third level decision tree 250. Within each level of the decision tree a set of nodes are present where each node corresponds to a particular evaluation (i.e. one node per rule) that will be conducted. Further, each node can have a user defined optional gain that conveys the importance of the node and its associated rule. Given a set of weights that are user defined, the expert system interprets the sum total correlation functions in succession through the propagation of the decision levels. The measure of the correlation function per decision level forms the criteria for the propagation to the following levels of processing or to terminate. This is conducted by the first terminal state detected 244, second terminal state detected 248, and the third terminal state detected 252 decision points. A YES from the terminal state detected caused by a diverging sum total correlation function per decision level conveys an abnormality of the joint under inspection and the next step would be to proceed to the fail 260 result. If however, a NO from the terminal state is detected, as a result of converging sum total correlation function per decision level, then this causes the processing to proceed to the next level of the expert system decision tree analysis. The final outcome of the expert system 188 is a pass 258 or a fail 260 result. The construction of decision trees can be complex, but it has been determined that simple decision trees are manageable and can be iteratively optimized to the desired performance of inspection. However, a manufacturing process that uses differing variables and techniques of production will require a modification of the weighting levels of the decision tree.

An alternate embodiment for the expert system 188 is the incorporation of a neural network 242. A neural network 242 is operated in parallel with the first level decision tree 240 to reinforce the outcome of a first terminal state detected 244. Such reinforcement provides a fail-safe added capability to the inspection system 10. A neural network also may be added in parallel with the second level decision tree 246 and the third level decision tree 250. A misrepresentation of the inspection system 10 results can occur if the user has inadvertently introduced errors in the construction of the weighting functions. Several neural network paradigms have been constructed, namely Back-Propagation, Nestor, and Adaptive Resonance Theory Type 2 readily known to one skilled in the art. The preferred paradigm is Nestor because of the ease of training the network. A network implemented with a limited number of neurons is suitable for rudimentary decision making process conducted at the first level decision tree 240. For the second and third level decision trees 246, 250, the network would require more neurons. The neural network 242 resides in the computer accelerator 47 segment of the computer 46.

This concludes the description of the preferred embodiment. However, many modifications and alterations will be obvious to one of ordinary skill in the art without departing from the spirit and scope of the inventive concept. Therefore, it is intended that the scope of this invention be limited only by the appended claims.

What is claimed is:

1. Apparatus for inspection of surface mount solder joints of an electronic module comprising:

means for positioning and aligning said module during said inspection;

a first light source means for providing a dark field illumination to non-flat surfaces of said module on said positioning means;

a first sensing means disposed above said first light source means for sensing an intensity of reflected light from said first light source to obtain a first image;

a second light source means for providing a bright field illumination to flat surfaces of said module on said positioning means;

a second sensing means disposed above said second light source means for sensing an intensity of reflected light from said second light source to obtain a second image;

processing means for compensating said first image for nonuniformities resulting from said first light source means and said first sensing means and for compensating said second image for nonuniformities resulting from said second light source means and said second sensing means;

means included in said processing means for providing information describing predetermined shadows to said detecting and compensating means using a PCB module data base and said second compensated image to compensate for predetermined shadows;

means included in said processing means for differentiating between a low light intensity region of said first image and said predetermined shadows of said first image;

means included in said processing means for detecting and compensating for said predetermined shadows resulting from surface mount components attached to said electronic module and said first light source means, said shadows including omni-directional and uni-directional shadows;

means included in said processing means for performing a transposition on said first image and said second image for establishing a three-dimensional topography of said module; and means included in said processing means for analyzing said three-dimensional topography and said intensity of said first image and said second image to determine the condition of said module.

2. The apparatus as recited in claim 1 wherein:

said positioning means comprises means for moving said module in an X-axis and a Y-axis directions.

3. The apparatus as recited in claim 2 wherein:

said positioning means comprises means for moving said module in a circular direction.

4. The apparatus as recited in claim 1 wherein:

said apparatus comprises means coupled to said first sensing means and said second sensing means for transferring said first image and said second image to said processing means.

5. The apparatus as recited in claim 1 wherein:

said means for performing a transposition comprises conversion of said intensity of said first image and said second image to a surface angle representation.

6. The apparatus as recited in claim 1 wherein:

said means for performing a transposition comprises means for performing a gradient analysis, a component interconnect boundary detection, a supervised segmentation and histogram analysis in predefined windows, an unsupervised segmentation connectivity analysis and a circular feature identification on said first image and said second image for establishing said three dimensional topography.

7. The apparatus as recited in claim 1 wherein:

said means for analyzing said three-dimensional topography comprises means for comparing said established three-dimensional topography to a predetermined three-dimensional topography criteria.

8. The apparatus as recited in claim 6 wherein:

said analyzing means further comprises an expert system having a plurality of decision levels.

9. The apparatus as recited in claim 7 wherein said analyzing means comprises an expert system having a neural network means.

10. The apparatus as recited in claim 1 wherein:

said means for analyzing said three-dimensional topography comprises means for determining a defective condition of solder connections, components, and printed circuit materials of said module.

11. The apparatus as recited in claim 1 wherein:

said first light source means comprises a plurality of ring lamps.

12. The apparatus as recited in claim 11 wherein:

said apparatus further comprises means for individually activating each of said plurality of ring lamps in accordance with a control signal generated by said processing means.

13. The apparatus as recited in claim 11 wherein:

said apparatus comprises means for activating said ring lamps simultaneously in accordance with a control signal generated by said processing means.

14. An automated vision inspection system comprising:

a computer means for controlling the operation of said vision inspection system;

a positioning table having a plurality of axes for positioning and aligning a module during an inspection in accordance with a command signal from said computer means;

a dark field illumination means positioned above said module for illuminating non-flat surfaces of said module;

a first camera disposed above said dark field illumination means for sensing an intensity of reflected light from said module to obtain a first image;

a bright field illumination means positioned above said module and adjacent to said dark field illumination means for illuminating flat surfaces of said module;

a second camera disposed above said bright field illumination means for sensing an intensity of reflected light from said module to obtain a second image;

processing means within said computer means for compensating said first image for nonuniformities from said dark field illumination means and said first camera and for compensating said second image for nonuniformities resulting from said bright field illumination means and said second camera;

means included in said processing means for providing information describing predetermined shadows to said detecting and compensating means using a PCB module data base to compensate for said predetermined shadows;

means included in said processing means for differentiating between a low light intensity region of said first image and said predetermined shadows of said first image;

means included in said processing means for detecting and compensating for said predetermined shadows resulting from surface mount components attached to an electronic module and said dark field illumination means, said shadows including omni-directional and uni-directional shadows;

means included in said processing means for performing a transposition on said first image and said second image for establishing a three-dimensional topography of said module;

means for comparing said established three-dimensional topography to a predetermined three-dimensional topography criteria; and expert system means for analyzing the results of said comparing means to detect a defect in said module.

15. The automated vision inspection system as recited in claim 17 wherein:

said positioning table comprises means for moving said module in an X-axis and a Y-axis directions.

16. The automated vision inspection system as recited in claim 14 wherein:

said positioning table comprises means for moving said module in a circular direction.

17. The automated vision inspection system as recited in claim 14 wherein:

said inspection system comprises means coupled to said first sensing means and said second sensing means for transferring said first image and said second image to said computer means.

18. The automated vision inspection system as recited in claim 14 wherein:

said means for performing a transposition comprises conversion of said intensity of said first image and said second image to a surface angle representation.

19. The automated vision inspection system as recited in claim 14 wherein:

said means for performing a transposition comprises means for performing a gradient analysis, a component interconnect boundary detection, a supervised segmentation and histogram analysis in predefined windows, an unsupervised segmentation connectivity analysis, and a circular feature identification on said first image and said second image for establishing said three dimensional topography.

20. The automated vision inspection system as recited in claim 14 wherein:

said expert system means comprises a plurality of decision levels.

21. The automated vision inspection system as recited in claim 14 wherein:

said expert system means comprises a neural network means.

22. The automated vision inspection system as recited in claim 14 wherein:

said expert system determines a defective condition of solder connections, components, and printed circuit materials of said module.

23. The automated vision inspection system as recited in claim 14 wherein:

said dark field illumination means comprises a plurality of ring lamps.

24. The automated vision inspection system as recited in claim 23 wherein:

said system further comprises means for individually activating each of said plurality of ring lamps in accordance with a control signal generated by said computer means.

25. The automated vision inspection system as recited in claim 23 wherein:

said system comprises means for activating said ring lamps simultaneously in accordance with a control signal generated by said computer means.

26. A method for inspection of surface mount solder joints of an electronic module comprising the steps of:

positioning and aligning said module for said inspection with a positioning means having a plurality of axes;

illuminating non-flat surfaces of said module with a first light source having a dark field illumination means positioned above said module;

sensing an intensity of reflected light from said first light source with a first sensing means to obtain a first image;

repositioning said module for said inspection;

illuminating flat surfaces of said module with a second light source having a bright field illumination means positioned above said module and adjacent to said first light source;

sensing an intensity of reflected light from said second light source with a second sensing means to obtain a second image;

compensating in a processing means said first image for nonuniformities resulting from said first light source and compensating said second image for nonuniformities resulting from said second light source and said second sensing means;

providing information describing predetermined shadows to said detecting and compensating means with means included in said processing means using a PCB module data base to compensate for said predetermined shadows;

differentiating in said processing means between a low light intensity region of said first image and said predetermined shadows of said first image;

detecting and compensating in said processing means for said predetermined shadows resulting from surface mount components attached to said electronic module and said first light source means, said, shadows including omni-directional and uni-directional shadows;

performing in said processing means a transposition on said first image and said second image for establishing a three-dimensional topography of said module; and analyzing said three-dimensional topography and said intensity of said first image and said second image in said processing means to determine the condition of said module.

27. The method as recited in claim 26 wherein:

said step of positioning said module comprises moving said module in an X axis and a Y axis direction.

28. The method as recited in claim 26 wherein:
said step of positioning said module comprises moving said module in a circular direction.

29. The method as recited in claim 26 wherein:
said steps of sensing an intensity of reflected light from said first light source and said second light source to obtain said first image and said second image comprises the steps of transferring said first image and said second image to a processing means.

30. The method as recited in claim 26 wherein:
said step of performing a transposition comprises the step of converting said intensity of said first image and said second image to a surface angle representation.

31. The method as recited in claim 26 wherein:
said step of performing a transposition comprises the steps of performing a gradient analysis, a component interconnect boundary detection, a supervised segmentation and histogram analysis in predefined windows, an unsupervised segmentation connectivity analysis, and a circular feature identification on said first image and said second image for establishing said three dimensional topography.

32. The method as recited in claim 26 wherein:
said step of analyzing said three-dimensional topography comprises the step of comparing said established three-dimensional topography to a predetermined three-dimensional topography criteria.

33. The method as recited in claim 32 wherein:
said step of analyzing said established three dimensional topography to a predetermined three dimensional criteria comprises the step of employing an expert system comprising a plurality of decision levels.

34. The method as recited in claim 32 wherein:
said step of analyzing said established three dimensional topography to a predetermined three dimensional criteria comprises the step of employing an expert system comprising a neural network means.

35. The method as recited in claim 26 wherein:
said step of determining the condition of said module includes detecting a defective condition in devices, solder connections and printed circuit materials.

36. The method as recited in claim 26 wherein:
said step of illuminating said module with a first light source includes said first light source having a plurality of ring lamps.

37. The method as recited in claim 36 wherein said step of illuminating said module with a plurality of ring lamps further comprises the step of individually activating each of said ring lamps in accordance with a control signal from said processing means.

38. A method of inspecting surface mount solder joints of an electronics module with an automated vision inspection system comprising the steps of:
controlling the operation of said vision inspection system with a computer means;
positioning a module during an inspection in accordance with a command signal from said computer means to a positioning table having a plurality of axes;
aligning said positioned module to a first camera and to a second camera;.
illuminating non-flat surfaces of said module with a dark field illumination means positioned above said module;
sensing an intensity of reflected light from said module to obtain a first image using said first camera disposed above said dark field illumination means;
illuminating flat surfaces of said module with a bright field illumination means positioned above said module and adjacent to said dark field illumination means;
sensing an intensity of reflected light from said module to obtain a second image using said second camera disposed above said bright field illumination means;
compensating said first image for nonuniformities from said dark field illumination means and said first camera and compensating said second image for non uniformities resulting from said bright field illumination means and said second camera with a processing means within said computer means;
providing information describing predetermined shadows to said processing means using a PCB module data base to compensate for said predetermined shadows;
differentiating in said processing means between a low light intensity region of said first image and said predetermined shadows of said first image;
performing detection and compensation in said processing means for said predetermined shadows resulting from surface mount components attached to said electronic modules and said dark field illumination means, said shadows including omni-directional and uni-directional shadows;
performing in said processing means a transposition on said first image and said second image for establishing a three-dimensional topography of said module;
comparing said established three-dimensional topography to a predetermined three-dimensional topography criteria; and
analyzing the results of said comparing means to detect a defect in said module with an expert system means.

39. The automated vision inspection system method as recited in claim 38 wherein:
said step of positioning said module comprises the steps of moving said module in an X-axis and a Y-axis directions.

40. The automated vision inspection system method as recited in claim 38 wherein:
said step of positioning said module comprises the step of moving said module in a circular direction.

41. The automated vision inspection system method as recited in claim 38 wherein:
said step of sensing an intensity of reflected light from said first light source and said second light source to obtain said first image and said second image comprises the steps of transferring said first image and said second image to said computer means.

42. The automated vision inspection system method as recited in claim 38 wherein:
said step of performing a transformation comprises the step of converting said intensity of said first image and said second image to a surface angle representation.

43. The vision inspection system as recited in claim 38 wherein:
said step of performing a transposition comprises the steps of performing a gradient analysis, a component interconnect boundary detection, a supervised segmentation and histogram analysis in predefined windows, an unsupervised segmentation connectivity analysis, and a circular feature identification on said first image and said second image for establishing said three dimensional topography.

44. The vision inspection system as recited in claim 38 wherein:

said step of analyzing with an expert system means comprises a plurality of decision level steps.

45. The automated vision inspection system method as recited in claim 38 wherein:

said step of analyzing with an expert system means comprises a step of analyzing with a neural network means.

46. The automated vision inspection system method as recited in claim 38 wherein:

said step of analyzing with said expert system determines a defective condition of solder connections, components, and printed circuit materials of said module.

47. The automated vision inspection system method as recited in claim 38 wherein:

said step of illuminating non-flat surfaces of said module with a dark field illumination means comprises the step of illuminating a plurality of ring lamps.

48. The automated vision inspection system method as recited in claim 47 wherein:

said step of illuminating said plurality of ring lamps comprises the steps of sequentially activating each of said plurality of ring lamps in accordance with a control signal generated by said computer means.

49. The vision inspection system as recited in claim 55 wherein:

said step of illuminating said plurality of ring lamps comprises activating said ring lamps simultaneously in accordance with a control signal generated by said computer means.

50. The apparatus as recited in claim 1 wherein:

said means for detecting and compensating for shadows comprises correcting a reduction in intensity of said first image due to shadows by increasing said intensity by an equivalent amount.

51. The method as recited in claim 26 wherein:

said step of detecting and compensating in said processing means for shadows resulting from said first light source means comprises the step of correcting a reduction in intensity of said first image due to shadows by increasing said intensity of said first image by an equivalent amount.

52. The automated vision inspection system method as recited in claim 38 wherein:

said step of performing detection and compensation in said processing means for shadows resulting from said dark field illumination means further comprises the step of correcting a reduction in intensity of said first image due to shadows by increasing said intensity of said first image by an equivalent amount.

* * * * *